US007273847B2

(12) United States Patent
McCormack, Jr.

(10) Patent No.: US 7,273,847 B2

(45) Date of Patent: Sep. 25, 2007

(54) PEPTIDES WITH ANTIOXIDANT AND ANTIMICROBIAL PROPERTIES

(76) Inventor: Francis X. McCormack, Jr., 706 Park Ave., Terrace Park, OH (US) 45174

( * ) Notice: Subject to any disclaimer, the term of this patent is extended or adjusted under 35 U.S.C. 154(b) by 369 days.

(21) Appl. No.: 10/312,829

(22) PCT Filed: Jun. 29, 2001

(86) PCT No.: PCT/US01/21226

§ 371 (c)(1),
(2), (4) Date: Aug. 4, 2003

(87) PCT Pub. No.: WO02/06301

PCT Pub. Date: Jan. 24, 2002

(65) Prior Publication Data

US 2004/0037781 A1 Feb. 26, 2004

Related U.S. Application Data

(60) Provisional application No. 60/215,313, filed on Jun. 30, 2000.

(51) Int. Cl.
*A61K 38/16* (2006.01)
*A61K 38/02* (2006.01)

(52) U.S. Cl. ............................. 514/12; 514/13; 514/21

(58) Field of Classification Search ..................... None
See application file for complete search history.

(56) References Cited

U.S. PATENT DOCUMENTS

| | | | | |
|---|---|---|---|---|
| 4,571,334 | A | 2/1986 | Yoshida et al. | 424/557 |
| 4,659,805 | A * | 4/1987 | Schilling et al. | 530/350 |
| 5,299,566 | A | 4/1994 | Davis et al. | 128/200.24 |
| 5,993,809 | A | 11/1999 | Weaver et al. | 424/94.61 |

FOREIGN PATENT DOCUMENTS

WO WO9950286 10/1999

OTHER PUBLICATIONS

Kaser et al. Inhibition of Bacterial Growth by Synthetic SP-$B_{178}$Peptides. Peptides. 1997, vol. 18, No. 9, pp. 1441-1444, especially the abstract, p. 1443, col. 2, second full paragraph.

* cited by examiner

*Primary Examiner*—Jeffrey Edwin Russel
(74) *Attorney, Agent, or Firm*—Dinsmore & Shohl LLP

(57) ABSTRACT

Methods of treating conditions associated with lipid oxidation or microbial proliferation include the step of administering a composition comprising a pharmacologically effective amount of an antioxidant or antimicrobial lung surfactant protein compound. Peptides derived from lung surfactant protein compounds possess lipid oxidation inhibiting and/or antimicrobial properties.

2 Claims, 13 Drawing Sheets

Fig. 6

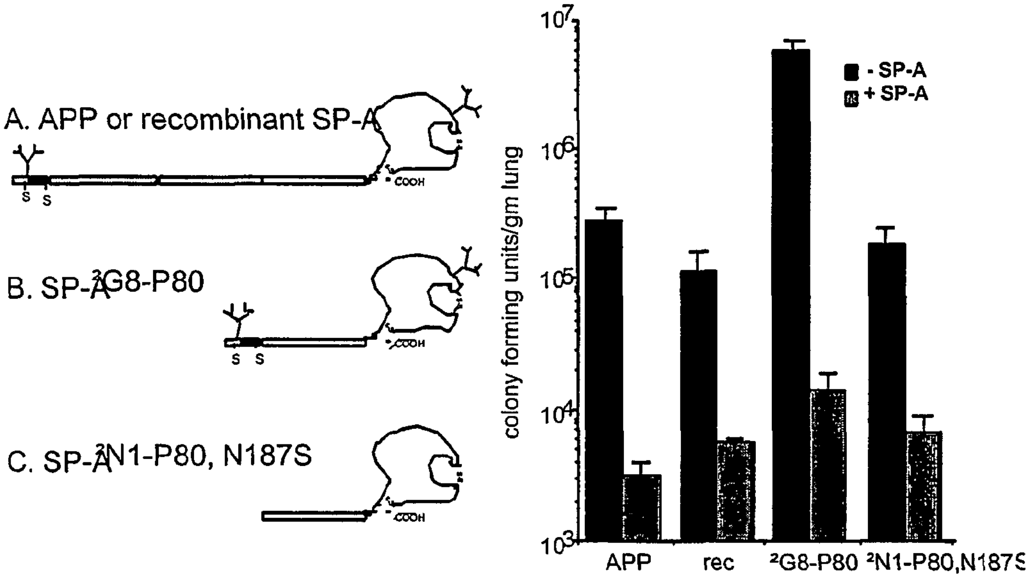

The N-terminal domains of SP-A are not required for GBS clearance. SP-A$^{-/-}$ mice were intratracheally inoculated with $10^4$ GBS in the presence of absence of 100 μg APP SP-A, recombinant SP-A (A) or truncated forms of SP-A containing deletions of the collagen-like domain (B) or all domains N-terminal to the neck plus the CHO domain(C). At 6 hrs post inoculation, CFU were quant-ified in lung homogenates.

SP-A and SP-D attenuate light scattering by growing E. coli but not GBS (above). E. coli (A,B, D) or Group B Strep (C) were grown at 37° C in the presence or absence of various quantities of SP-A (A, B, C) or SP-D ( D) and light scattering ($A_{400}$)was measured in a spectrophotometer. J5 LPS vesicles were added in some tubes (C,D). Data are n = 3-5 ± S.E.

SP-A and SP-D inhibit the growth of E. coli. Agar imbedded E.coli K12 were grown overnight at 37°C in the presence of 0.5 or 5.0 μg SP-A, SP-D or control proteins. In some experiments, the collectins (0.5 μg) were preincubated with specific antibody (5 μg) (B) or J5 LPS vesicles (750 ng)(C) before addition to the wells.

The N-terminal domains of SP-A are not required for growth inhibition (Upper left panel). E. coli K12 organisms were exposed to lysozyme (5,.5,.5,5μg right to left), SP-A containing a deletion of the N-terminal domains (ΔAsn1-Pro80) (.5,5,5,5,.5μg), rat SP-A (.5,5,5,5,.5μg) or albumin (5,5 μg).

Fig. 10

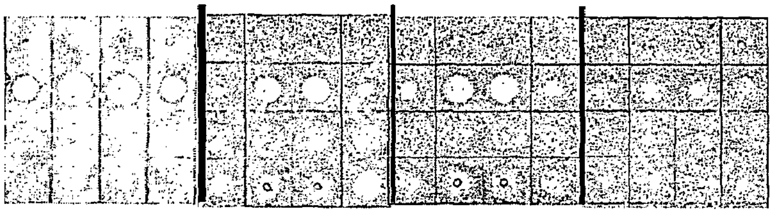

Outer membrane porin A protects E. coli from growth inhibition by SP-A and SP-D. (Upper right panel) Isogenic mutant E. coli derived from clinical isolate parental strain E69 were exposed to 0.5 or 5 μg collectins (denoted above lanes) in a radial diffusion assay. Mutants with OmpA deficiency (ΔOmpA), plasmid driven OmpA overexpression in ΔOmpA background and ΔOmpA containing empty plasmid are shown shown.

SP-A inhibits protein synthesis in H. capsulatum (Upper left panel). Histoplasma capsulatum were grown in rich media containing 0-250 μg/ml APP-SP-A for 24 hrs, followed by incubation with $^3$H-leucine for an additional 24 hours. Proteins were captured on fiberglass filters and counted in a scintillation counter. Data are from one representative experiment of two.

Fig. 12

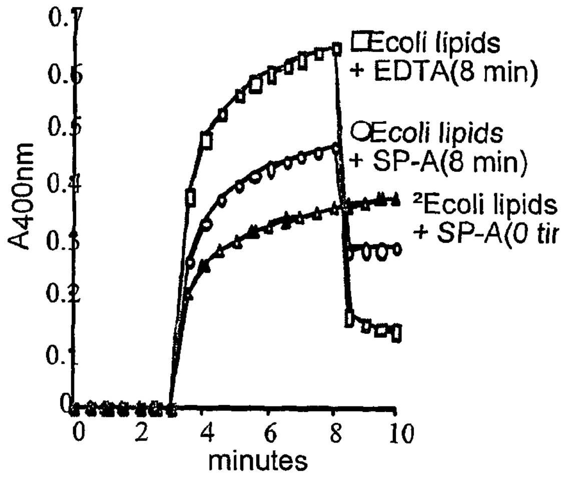

SP-A inhibits and reverses $Ca^{2+}$ dependent aggregation of unilamellar liposomes composed of E. coli lipids. (Upper right panel) Unilamellar vesicles composed of phospholipids purified from E. coli (Avanti, approx. 67% PE, 23% PG and 10% Cardiolipin) were generated by sonication, loaded in cuvettes (200 μg/ml) and aggregated by addition of 5 mM $Ca^{2+}$. EDTA was added at 8 minutes in one cuvette (□), and SP-A (10 μg/ml) was added at time 0 (Δ) or at 8 minutes in the others(μ). Data are from one representative experiment of three.

Fig. 13

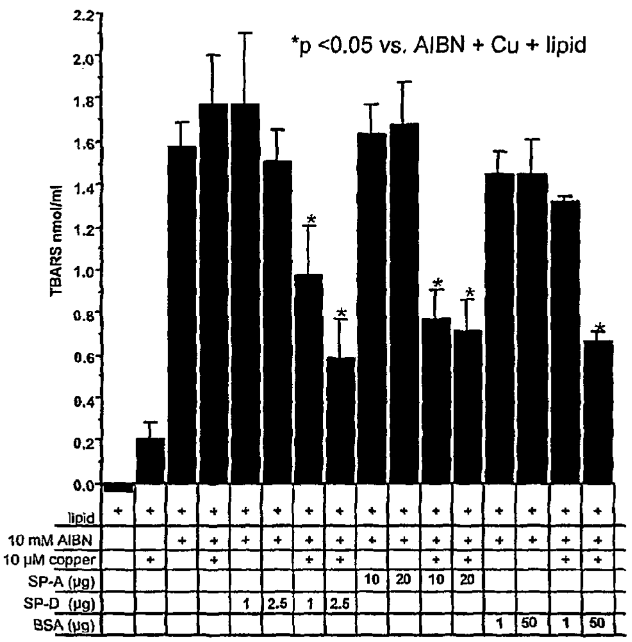

Inhibition of AIBN-induced lipid peroxidation by SP-A and SP-D requires complex formation with copper. Liposomes composed of 18:0;18:2 phosphatidylcholine were exposed to the free radical generator azobis 2,2'-azobisisobutyronitrile (AIBN) for three hours at 37°C. Surfactant proteins A (SP-A) or (SP-D), or the control protein bovine serum albumin (BSA) were added at the indicated concentrations in the presence or absence of 10 μM copper. Oxidation was measured using the TBARS assay. T-test comparisons between TBARS generated by lipid + AIBN + copper vs. lipid + AIBN + copper + protein were considered significant if $p < 0.05$.

PEPTIDES WITH ANTIOXIDANT AND ANTIMICROBIAL PROPERTIES

RELATED APPLICATION

The present application claims priority under 35 U.S.C. § 119 of U.S. Provisional Application Ser. No. 60/215,313 filed Jun. 30, 2000, the entire disclosure which is herein incorporated by reference.

This invention was made with government support under Grant No. HL-61612 awarded by the National Institutes of Health. The government has certain rights in the invention.

BACKGROUND OF THE INVENTION

The present invention relates generally to methods for reducing or preventing the oxidation of lipids or other molecules, and to methods for inhibiting or reducing microbial proliferation. Specifically, the present invention is directed to compositions and methods for treating oxidative lung injury and other oxidative disorders, and to methods for preventing oxidation of foods, cosmetics and medications. Additionally, the present invention is directed to compositions and methods for treating lung infection and other disorders caused by microbial infection.

The lung is made up of a series of branching conducting airways that terminate in grape-like clusters of delicate gas exchanging airspaces called pulmonary alveoli. Maintenance of alveolar patency at end expiration requires pulmonary surfactant, a mixture of saturated and unsaturated phospholipids and proteins that lines the epithelial surface and reduces surface tension. Surfactant is presented to the oxidizing effects of atmospheric oxygen and inhaled toxicants over a tennis court-sized interface with the environment. The pathophysiological consequences of surfactant oxidation in humans and experimental animals exposed to hyperoxia include airspace collapse, reduced lung compliance and impaired gas exchange.

Air breathing is made possible through the surface tension lowering properties of lung surfactant, an oily film located at the boundary between the aqueous pulmonary epithelial lining fluid (ELF) and the air in the lumen of the alveoli, the gas exchanging distal airspaces of the lung. By weight, surfactant is composed of approximately 50% saturated phospholipids, 40% unsaturated phospholipids and 10% protein, including hydrophilic surfactant proteins A (SP-A) and D (SP-D), and the hydrophobic surfactant proteins B (SP-B) and C (SP-C). After secretion into the ELF, the components of surfactant form membranes at the air-liquid interface which spread readily and compress poorly during cyclical respiratory expansion and contraction.

These properties of surfactant result in enhanced lung compliance during inspiration, which reduces the work of breathing, and very low alveolar surface tension at end expiration, which helps to maintain airspace patency. Exposure of surfactant to ambient oxygen and potent environmental oxidants such as ozone can result in peroxidation of unsaturated phospholipids, surfactant inactivation, airspace collapse and impaired gas exchange. Antioxidant protection of surfactant phospholipids in the ELF has classically been attributed to low molecular mass components urate, ascorbate, and reduced glutathione, and to proteinaceous antioxidants albumin, superoxide dismutase and catalase.

Moreover, after secretion by alveolar type II cells and nonciliated bronchiolar cells into the alveolar lining layer (ALL), the components of surfactant form phospholipid enriched membranes at the air-liquid interface. The surfactant lining has critical surface tension lowering properties which reduce the work of breathing and help to maintain airspace patency. However, the surfactant layer also places a hydrophobic barrier between the inhaled organism and the antimicrobial defenses of the pulmonary epithelium and ALL. In the absence of any specialized defense mechanisms positioned in and around the surfactant membrane, the organism could theoretically proliferate in a microenvironment free from the threat of phagocytic cells, specific antibodies, or innate immune antimicrobial peptides. Without being bound by theory, it is believed that the hydrophilic protein components of the surfactant lining layer, SP-A and SP-D, have potent macrophage independent antimicrobial properties.

The oxidative modifications of surfactant lipids and low density lipoproteins (LDL) and/or microbial proliferation represent key events in the pathogenesis of tissue injury. Thus there is a need for useful therapeutical application of compounds with antioxidant properties and/or antimicrobial properties in the treatment of the inflammatory and hyperoxic lung disease, atherosclerosis, oxidative injury to the skin, and/or lung infection or injury. There is also a need to prevent spoilage, off flavors and off colors due to oxidation and/or microbial proliferation in foods, cosmetics and medications.

SUMMARY OF THE INVENTION

An object of the invention is to provide methods for inhibiting the oxidation of lipids, proteins and other compounds. An additional object is to provide methods for treating conditions associated with microbial contamination, colonization or infection. Another object of the present invention is to provide methods and compositions for treating a mammal having a condition associated with oxidative tissue injury, such as oxidative lung injury, aging of the skin or atherosclerosis. Similarly, another object of the present invention is to provide methods for inhibiting a macrophage-independent microbial proliferation in mammals with lung infection or injury, or systemic or local infections. Yet another object of the invention is to provide compositions and methods for the treatment of acute lung injury, including adult respiratory distress syndrome and hyperoxic lung injury.

One aspect of the invention is the prevention of oxidation in food, pharmaceutical compositions, cosmetic preparations and dermatological preparations. Similarly, another aspect of the invention is the prevention of microbial proliferation in food, pharmaceutical compositions, cosmetic preparations and dermatological preparations.

Another object of the invention is to provide pharmacological compositions comprising antioxidant or antimicrobial lung surfactant protein compounds. One method of inhibiting lipid oxidation or microbial proliferation is by intratracheal, dermal or oral administration of an antioxidant or antimicrobial lung surfactant protein compound to a mammal, preferably a human.

In one embodiment, pharmacological compositions may comprise an antioxidant or antimicrobial lung surfactant protein compound and, optionally, pharmaceutically acceptable carriers, fillers or excipients. In another embodiment, a method of treating a mammal, preferably a human, comprises administering to the mammal a pharmacological composition comprising an antioxidant or antimicrobial lung surfactant protein compound and, optionally, pharmaceutically acceptable carriers, fillers or excipients.

The methods also comprise administering an antioxidant or antimicrobial lung surfactant protein compound along with a lipophilic solvent or carrier. The lipophilic solvent or carrier may be an organic solvent, phosphatidylcholine, cholesterol, or surfactant phospholipid.

The lung surfactant proteins may be used as ingredients of medications or foods to prevent lipid oxidation and/or microbial proliferation of those reagents, or as ingredients of cosmetics to prevent spoilage of the product or to provide antioxidant or antimicrobial effects on skin and hair. The surfactant proteins may have advantages over antioxidant ingredients such as butylated hydroxytoluene (BHT) or antimicrobial ingredients such as thimerosal for the preparation of all-natural products, since they are derived from animal sources, are edible and are nontoxic.

A number of novel peptides derived from rat lung surfactant proteins SP-A and SP-D possess lipid oxidation inhibiting and/or antimicrobial properties that are similar to the full length molecules. Similarly, novel lipid oxidation suppressant and antimicrobial peptides may be derived from human lung surfactant proteins SP-A and SP-D. When administered by aerosol or by intratracheal instillation, these truncated proteins can be used to decrease lung injury due to hyperoxia, inflammation or infection. When included as ingredients in foods, cosmetics and medications, the truncated proteins can inhibit lipid oxidation or microbial proliferation that produces spoilage, off colors and off flavors. Compared to full length proteins, these peptides are more easily manufactured in quantities that are practical for therapeutic use, or as ingredients in foods, cosmetics and medications. Without being limited by theory, however, it is believed that immunogenicity problems associated with administration of peptides to humans should be limited, since they will comprise specific portions of the native human lung surfactant protein compound proteins.

Other objects, features and advantages of the present invention will become apparent from the following detailed description. It should be understood, however, that the detailed description and the specific examples, while indicating several preferred embodiments of the invention, are given by way of illustration only, since various changes and modifications within the scope of the invention will become apparent to those skilled in the art from this detailed description.

BRIEF DESCRIPTION OF THE FIGURES

While the specification concludes with claims particularly pointing out and distinctly claiming the present invention, it is believed that the same will be understood from the following description taken in conjunction with the accompanying drawings in which:

FIG. 6 depicts the N-terminal domains of SP-A as related to GBS clearance;

FIG. 10 depicts the protection of *E. coli* from growth inhibition in the presence of SP-A and SP-D by the outer membrane porin A;

FIG. 12 depicts the inhibition and reversal of $Ca^{2+}$ dependent aggregation of unilamellar liposomes composed of *E. coli* lipids in the presence of SP-A; and FIG. 13 depicts the inhibition of AIBN-induced lipid peroxidation by SP-A and SP-D regarding complex formation with copper.

DETAILED DESCRIPTION OF THE INVENTION

Figure 1:
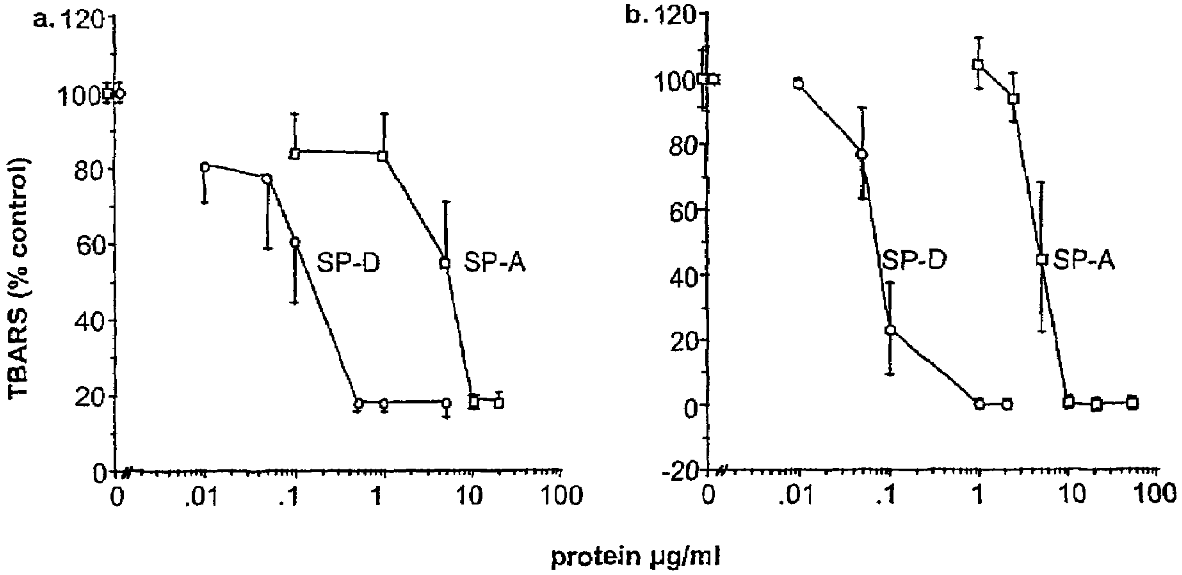
FIG. 1 depicts the inhibition of copper-induced lipid oxidation by SP-A and SP-D as measured by a thiobarbituric reactive substances (TBARS) assay.

The hydrophilic surfactant proteins, SP-A and SP-D, according to the present invention directly protect surfactant phospholipids and alveolar macrophages from oxidative modification and injury and directly inhibit microbial growth. The antioxidant and antimicrobial activities associated with SP-A maps to the carboxy terminal domain of the protein, which like SP-D, contains a C-type lectin carbohydrate recognition domain (CRD). As a result, surfactant proteins SP-A and SP-D, which are ubiquitous among air breathing organisms, contribute to the protection of the lung from oxidative stresses due to atmospheric or supplemental oxygen, air pollutants and lung inflammation, while further protecting the lung from inhaled organisms.

The hydrophilic surfactant proteins, SP-A and SP-D, have potent, direct phospholipid antioxidant properties. In particular, they show the capability to prevent and/or to delay the oxidative modification of surfactant phospholipids and LDL. Additionally, the inventors of the present invention believe, without being limited by theory, that the mechanism of action of the antioxidant function competes with the chain of propagation of the lipid peroxidation through an effective scavenging of the peroxylic radicals.

Additionally, SP-A and SP-D, have been found to have potent, macrophage independent antimicrobial properties. In particular, they show the capability to prevent and/or to delay the proliferation of various species of *E. coli, P. aeruginosa*, and the dimorphic fungus *Histoplasma Capsulatum.*

The hydrophilic surfactant proteins, and derivatives, analogs, homologs, salts and fragments thereof, as well as lipid oxidation inhibiting and antimicrobial peptides, which substantially correspond in sequence to the amino acid sequence found in specific portions of SP-A or SP-D, can find useful therapeutical application in the treatment of the inflammatory and hyperoxic lung disease, atherosclerosis or oxidative injury to the skin; and in preventing spoilage, off flavors and off colors in foods and cosmetics. Additionally, the antimicrobial properties found in the specific portions of SP-A or SP-D, are useful in treating inflammatory and infectious lung diseases, as well preventing spoilage, off flavors and off colors in foods and cosmetics. The present invention also provides compositions for lipid oxidation inhibition and microbial proliferation in animals, including man As used herein, "lung surfactant protein compounds" is intended to refer to proteins found in lung surfactant, and includes derivatives, analogs, homologs, salts and fragments thereof. Antioxidant lung surfactant protein compounds are lung surfactant protein compounds and derivatives, analogs, homologs, salts and fragments thereof, which have antioxidant properties. Preferably, the antioxidant lung surfactant protein compounds have phospholipid antioxidant properties. Antioxidant lung surfactant protein compounds include lipid oxidation inhibiting peptides, also referred to as antioxidant peptides, which substantially correspond in sequence to amino acid sequence found in specific portions of antioxidant lung surfactant protein compounds.

As used herein, "antimicrobial lung surfactant protein compounds" refers to lung surfactant protein compounds and derivatives, analogs, homologs, salts and fragments thereof, which have antimicrobial properties. Antimicrobial lung surfactant protein compounds include antimicrobial peptides which are defined as synthetic chains of up to 100 amino acids and fragments (portions of the native proteins), which substantially correspond in sequence to amino acid sequence found in specific portions of antimicrobial lung surfactant protein compounds.

Suitable lung surfactant protein compounds of the present invention are surfactant proteins A and D. Surfactant proteins A and D are members of the collectin family of preimmune opsonins that are thought to play a role in opsonization and clearance of pathogenic microorganisms. A comprehensive disclosure of pulmonary surfactants A and D may be found in: (Bridges J P, Damodarasamy M, Kuroki Y, Howles G, Hui D Y, McCormack F X. *Pulmonary surfactant proteins A and D are potent endogenous inhibitors of lipid peroxidation and cellular injury*, J Biol Chem 275:38848-38855, 2000), herein incorporated by reference in its entirety. All members of this family have similar overall structural organization including an N-terminal region containing two interchain disulfide bonds, a collagen-like region of gly-x-y repeats containing hydroxylated amino acids, an amphipathic helical neck region and a C-terminal, C-type carbohydrate recognition domain (CRD). Trimerization occurs by triple helix formation in the collagen-like domain and bundled alpha-helical coiled-coil formation in the neck region. SP-A assembles into a hexamer of trimers that are disulfide-linked at the N-terminus and laterally associated through the first portion of the collagen-like domain, forming a flower bouquet-like structure. SP-D forms a cruciform shaped oligomer of four trimers that are joined by disulfide bonds at the N-terminus. Experimental data suggest that SP-A protects surfactant from serum protein inhibitors, and contributes to the assembly and stability of surfactant membranes and the surfactant aggregate, tubular myelin. Both SP-A and SP-D appear to participate in host defense against diverse microbial species including bacteria, viruses, and fungi.

Suitable peptides of the present invention include peptides which correspond to specific areas of the lung surfactant protein compound and comprise at least a 93 amino acid sequence derived from the amino terminal portion of the mature lung surfactant protein compounds. Larger peptides of from about 148 to about 248 amino acids, each containing within its sequence the aforementioned repeat sequence, are also contemplated by the present invention.

In one embodiment an antioxidant lung surfactant protein compound or antimicrobial lung surfactant protein compound is a peptide comprising at least about 93, preferably at least about 96 amino acids. In one embodiment the antioxidant or antimicrobial lung surfactant protein compound is a peptide comprising from about 93 to about 248 amino acids, preferably from about 93 to about 148 amino acids, while in another embodiment the antioxidant or antimicrobial lung surfactant protein compound is a peptide comprising from about 96 to about 154 amino acids. In yet another embodiment the antioxidant or antimicrobial lung surfactant protein compound is a peptide comprising from about 5 to about 90, preferably from about 5 to about 30, amino acids. Furthermore, in still another embodiment, the antimicrobial lung surfactant protein compound is a peptide comprising from about 96 to about 375 amino acids (for SP-D).

Preferred antioxidant and/or antimicrobial lung surfactant protein compounds include peptides which substantially correspond in sequence to the portions of SP-A and SP-D which map to the antioxidant activity and/or the antimicrobial properties. In one embodiment the antioxidant or antimicrobial lung surfactant protein compound is selected from peptides which substantially correspond in sequence to the C-type lectin carbohydrate recognition domain of SP-A and peptides which substantially correspond in sequence to the C-type lectin carbohydrate recognition domain of SP-D.

In another embodiment the antioxidant or antimicrobial lung surfactant protein compound is selected from peptides which comprise at least a 93 amino acid sequence derived from the carboxyl terminal portion of SP-A or SP-D.

The peptides of the present invention may be linked to an additional sequence of amino acids by either or both the N-terminus and the C-terminus, wherein the additional sequences are from 1 to about 45 amino acids in length. Such additional amino acid sequences, or linker sequences can be conveniently affixed to a detectable label or solid matrix, or carrier. Labels, solid matrices and carriers that can be used with peptides of the present invention are described below. Typical amino acid residues used for linking are tyrosine, cysteine, lysine, glutamic acid and aspartic acid, or the like.

Lipid oxidation suppressant peptides and antimicrobial peptides derived from rat lung surfactant proteins or from human lung surfactant proteins possess lipid oxidation inhibiting or antimicrobial properties that are similar to the full length molecules. Suitable peptides are listed below, and are compared to the native molecule.

Surfactant Protein A

A1. Neck and CRD of rat SP-A (148 aa)

```
                                            (SEQ ID NO:2)
AYLDEELQTELYEIKHQILQTMGVLSLQGSMLSVGDKVSTNGQSVNFDTI

KEMCTFRAGGNIAVPRTPEENEAIASIAKKYNNYVYLGMIEDQTPGDFHY

LDGASVNYTNWYPGEPRGQGKEKCVEMYTDGTWNDRGCLQYRLAVCEF
```

A2. Smaller active fragment of rat SP-A (93 aa)

```
                                            (SEQ ID NO:3)
AYLDEELQTELYEIKHQILQTMGVLSLQGSMLSVGDKVSTNGQSVNFDTI

KEMCTFRAGGNIAVPRTPEENEAIASIAKKYNNYVYLGMIEDQ
```

A3. An active synthetic peptide derived from rat sequence (21 aa) Thr Pro Gly Asp Phe His Tyr Leu Asp Gly Ala Ser Val Asn Tyr Thr Asn Trp Tyr Pro Gly (SEQ ID NO:16)

A4. Human SP-A (248 aa)

```
                                            (SEQ ID NO:4)
MWLCPLALTLILMAASGAACEVKDVCVGSPGIPGTPGSHGLPGRDGRDGV

KGDPGPPGPMGPPGETPCPPGNNGLPGAPGVPGERGEKGEPGERGPPGLP
```

-continued

AHLDEELQATLHDFRHQILQTRGALSLQGSIMTVGEKVFSSNGQSITFDA

IQEACARAGGRIAVPRNPEENEAIASFVKKYNTYAYVGLTEGPSPGDFRY

SDGTPVNYTNWYRGEPAGRGKEQCVEMYTDGQWNDRNCLYSRLTICEF

A5. Active region of human SP-A-Neck and CRD of human SP-A (148 aa)

(SEQ ID NO:5)

AHLDEELQATLHDFRHQILQTRGALSLQGSIMTVGEKVFSSNGQSITFDA

IQEACARAGGRIAVPRNPEENEAIASFVKKYNTYAYVGLTEGPSPGDFRYS

DGTPVNYTNWYRGEPAGRGKEQCVEMYTDGQWNDRNCLYSRLTICEF

A6. An active fragment of human SP-A based on the rat SP-A data (93 aa)

(SEQ ID NO:6)

AHLDEELQATLHDFRHQILQTRGALSLQGSIMTVGEKVFSSNGQSITFDA

IQEACARAGGRIAVPRNPEENEAIASFVKKYNTYAYVGLTEGP

A7. An active synthetic peptide derived from human sequence (21 aa)

(SEQ ID NO:17)

Ser Pro Gly Asp Phe Arg Tyr Ser Asp Gly Thr Pro
Val Asn Tyr Thr Asn Trp Tyr Arg Gly

Surfactant Protein D

D1. Full length rat SP-D (374 aa)

(SEQ ID NO:7)

MLHFLSMLVLLVQPLGDLGAEMKTLSQRSITNTCTLVLCSPTENGLPGRD

GRDGREGPRGEKGDPGLPGPMGLSGLPGPRGPVGPKGENGSAGEPGPKGE

RGLVGPPGSPGISGPAGKEGPSGKQGMGPQGKPGPKGEAGPKGEVGAPGM

QGSAGAKGPAGPKGERGAPGEQGAPGNAGAAGPAGPAGPQGAPGSRGPPG

LKGDRGAPGDRGIKGESGLPDSAALRQQMEALNGKLQRLEAAFSRYKKAA

LFPDGQSVGDKLFRAANSEEPFEDAKEMCRQAGGQLASPRSATENAAVQQ

LVTAHSKAAFLSMTDVGTEGKFTYPTGEALVYSNWAPGEPNNNGGAENCV

EIFTNGQWNDKACGEQRLVICEF

D2. Neck and CRD of rat SP-D (the final 153 aa)

(SEQ IDNO:8)

DSAALRQQMEALNGKLQRLEAAFSRYKiKAALFPDGQSVGDKIFRAANSE

EPFEDAKEMCRQAGGQLASPRSATENAAVQQLVTAHSKAAFLSMTDYGTE

GKFTYPTGEALVYSNWAPGEPNNNGGAENCVEJFTNGQWNDKACGEQRLV

ICEF

D3. Human SP-D (375 aa)

(SEQ ID NO:9)

MLLFLLSALV LLTQPLGYLE AEMKTYSHRT MPSACTLVMC

SSVESGLPGR DGRDGREGPRGEKGDPGLPG AAGQAGMPGQ

-continued

AGPVGPKGDN GSVGEPGPKG DTGPSGPPGP

PGVPGPAGREGALGKQGNLG PQGKPGPKGE AGPKGEVGAP

GMQGSAGARG LAGPKGERGV PGERGVPGNTGAAGSAGAMG

PQGSPGARGP PGLKGDKGIP GDKGAKGESG LPDVASLRQQ

VEALQGQVQHLQAAFSQYKK VELFPNGQSV GEKIFKTAGF

VKPFTEAQLL CTQAGGQLAS PRSAAENAAL QQLVVAKNEA

AFLSMTDSKT EGKFTYPTGE SLVYSNWAPGEPNDDGGSED

CVEIFTNGKWNDRACGEKRLVVCEF

D4. Neck and CRD of human SP-D (the final 154 aa)

(SEQ ID NO:10)

DVASLRQQVEALQGQVQHLQAAFSQYKKVELFPNGQSGEKJFKTAGF

VKPFTEAQLLCTQAGGQLASPRSAAENAALQQLVVAKNEAAFLSMTDSKT

EGKFTYPTGESLVYSNWAPGEPNDDGGSEDCVEIFTNGKWNDRA

CGEKRLVVCEF

D5. An active fragment of human SP-D based on the rat SP-A data (96 aa near the C-terminus of the molecule)

(SEQ ID NO:11)

DVASLRQQVEALQGQVQHLQAAFSQYKKVELFPNGQSVGEKJFKTAGF
VKPFTEAQLLCTQAGGQLASPRSAAENAAIQQLVVAKNEAAYLSMTDS

In one embodiment of the invention, the lipid oxidation inhibiting peptides and antimicrobial peptides of the present invention substantially correspond to peptides having the amino acid sequences set forth in SEQ ID NOS:2-11 and 16-17, preferably SEQ ID NOS:4-6, 9-11 and 17.

In another embodiment of the invention, the lipid oxidation inhibiting peptides and the antimicrobial peptides of the present invention substantially correspond to the following amino acid sequences:

(SEQ ID NO:12)

MSLCSLAFTLFLTVVAGIKCNVTDVCAGSPGIPGAPGNHGLPGRDGRDGV

KGDPGPPGPMGPPGGMPGLPGRDGLPGAPGAPGERGDKGEPGERGLPGFP

AYLDEELQTELYEIKHQILQTMGVLSLQGSMLSVGDKVFSTNGQSVNFDT

IKEMCTRAGGNIAVPRTPEENEAIASJAKKYNNYVYLGMIEDQTPGDFHY

LDGASVNYTNWYPGEPRGQGKEKCVEMYTDGTWNDRGCLQYRLAVCEF (SEQ ID NO:13)

AYLDEELQTELYEIKHQILQTMGVLSLQGSMLSVGDKVFSTNGQSVNFDT

IKEMCTRAGGNIAVPRTPEENEAIASIAKKYNNYVYLGMIEDQTPGDFHY

LDGASVNYTNWYPGEPRGQGKEKCVEMYTDGTWNDRGCLQYRLAYCEF (SEQ ID NO:14)

MSLCSLAFTLFLTVVAGIKCNVTDVCAGSPGIPGAPGNHGLPGRDGRDGV

KGDPGPPGPMGPPGGMPGLPGRDGLPGAYGAYGERGDKGEPGERGLPGFP

AYLDEELQTELYEIKHQILQTMGVLSLQGSMLSVGDKVFSTNGQSVNFDT

JKEMCTRAGGNJAVPRTPEENEAIASIAKKYNNYVYLGMIED

-continued

```
                                          (SEQ ID NO:15)
AYLDEELQTELYEIKHQILQTMGVLSLQGSMLSVGDKVFSTNGQSVNFDT

IKEMCTRAGGNIAVPRTPEENEAIASIAKKYNNYVYLGMIED
```

as well as homologs and analogs thereof; wherein:

| |
|---|
| A = Ala = Alanine |
| R = Arg = Arginine |
| N = Asn = Asparagine |
| D = Asp = Aspartic acid |
| B = Asx = Asparagine or aspartic acid |
| C = Cys = Cysteine |
| Q = Gin = Glutamine |
| E = Glu = Glutamic acid |
| Z = Glx = Glutamine or Glutamic acid |
| G Gly = Glycine |
| H = His = Histidine |
| I = Ile = Isoleucine |
| L = Leu = Leucine |
| K = Lys = Lysine |
| F = Phe = Phenylalanine |
| P = Pro = Proline |
| S = Ser = Serine |
| T = Thr = Threonine |
| W = Trp = Tryptophan |
| Y = Tyr = Tyrosine |
| V = Val = Valine |

The one-letter symbols used to represent the amino acid residues in the peptides of the present invention are those symbols commonly used in the art.

In another embodiment of the invention, an antioxidant or antimicrobial peptide of the present invention substantially corresponds to the amino acid sequence selected from the group consisting of:

```
                                          (SEQ ID NO:1)
Met-Phe-Leu-Lys-Ala-Val-Val-Leu-Thr-Val-Ala-Leu-
Val-Ala-IUe-Thr-Gly-Thr-GIn-Ala-GLu-VaI-Thr-Ser-
Asp-Gln-Val-Ala-Asn-Val;

                                         (SEQ ID NO:16)
Thr Pro Gly Asp Phe His Tyr Leu Asp Gly Ala Ser
Val Asn Tyr Thr Asn Trp Tyr Pro Gly;

                                         (SEQ ID NO:17)
Ser Pro Gly Asp Phe Mg Tyr Ser Asp Gly Thr Pro Val
Asn Tyr Thr Asn Trp Tyr Mg Gly;
```

and mixtures thereof.

By “substantially corresponding” is meant an amino acid sequence having a homology to any of the listed sequences of about 70%.

As used herein, “peptide” refers to a linear series of amino acid residues connected to one another by peptide bonds between the alpha-amino and carboxy groups of adjacent amino acid residues. The term “synthetic peptide” is intended to refer to a chemically derived chain of amino acid residues linked together by peptide bonds and which is free of naturally occurring proteins and fragments thereof. Additionally, analogs, homologs, fragments, chemical derivatives and pharmaceutically acceptable salts of the novel peptides provided herein are included within the scope of the term “peptide”. In one embodiment of the invention an antioxidant or antimicrobial peptide comprises less than about 100 amino acid residues.

By “peptide analog” is meant a peptide which differs in amino acid sequence from the native peptide only by conservative amino acid substitutions, for example, substitution of Leu for Val, or Arg for Lys, etc., or by one or more non-conservative amino acid substitutions, deletions, or insertions located at positions which do not destroy the biological activity of the peptide (in this case, the ability of the peptide to target vascular lesions). A peptide analog, as used herein, may also include, as part or all of its sequence, one or more amino acid analogs, molecules that mimic the structure of amino acids, and/or natural amino acids found in molecules other than peptide or peptide analogs.

By “homologs” is meant the corresponding peptides derived from other known antioxidant or antimicrobial lung surfactant protein compound proteins having the same or substantially the same properties.

By “analogs” is meant substitutions or alterations in the amino acid sequences of the peptides of the invention, which substitutions or alterations do not abolish the antioxidant or antimicrobial properties of the peptides. Thus, an analog might comprise a peptide having a substantially identical amino acid sequence to a peptide provided herein as SEQ ID NO: 1 wherein one or more amino acid residues have been conservatively substituted with chemically similar amino acids. Examples of conservative substitutions include the substitution of a non-polar (hydrophobic) residue such as isoleucine, valine, leucine or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated.

Analogs may also encompass additional amino acids, added to the N- and/or C-terminal portion of the peptide. For example, analogs of the peptides of the invention may contain cysteine or another amino acid, at the amino or carboxyl end of the peptide by which the peptide may be covalently attached to a carrier protein, e.g., albumin, for in vivo administration. Other carrier molecules include polyethylene glycol (PEG) which functions to avoid proteolytic cleavage and clearing of peptides from the blood.

The phrase “conservative substitution” also includes the used of chemically derivatized residues in place of a non-derivatized residues as long as the peptide retains the requisite antioxidant or antimicrobial properties. Analogs also include the presence of additional amino acids or the deletion of one or more amino acids that do not affect biological activity. For example, analogs of the subject peptides may contain an N- or C-terminal cysteine, by which, if desired, the peptide may be covalently attached to a carrier protein, e.g., albumin. Such attachment, it is believed, will minimize clearing of the peptide from the blood and also prevent proteolysis of the peptides.)

The practice of the present invention employs, unless otherwise indicated, conventional techniques of synthetic organic chemistry, protein chemistry, molecular biology, microbiology, and recombinant DNA technology, which are well within the skill of the art. Such techniques are explained fully in the literature.

In preferred embodiments, the peptide or peptide analog is water soluble; or is soluble in a physiological fluid, preferably, one that is at physiological pH, for example, blood plasma.

In another preferred embodiment, the peptide has a molecular conformation analogous to the molecular conformation (size, shape, charge) of a surface region of the lung surfactant protein compounds moiety. Examples of peptides believed to have a molecular conformation analogous to the molecular conformation of a surface region of the lung surfactant protein include:

(SEQ ID NO:1)
Met-Phe-Leu-Lys-Ala-Val-Val-Leu-Thr-Val-Ala-Leu-Val-Ala-Ile-Thr-Gly-Thr-Gln-Ala-Glu-Val-Thr-Ser-Asp-Gln-Val-Ala-Asn-Val;

(SEQ ID NO:16)
Thr Pro Gly Asp Phe His Tyr Leu Asp Gly Ala Ser Val Asn Tyr Thr Asn Trp Tyr Pro Gly;

(SEQ ID NO:17)
Ser Pro Gly Asp Phe Arg Tyr Ser Asp Gly Thr Pro Val Asn Tyr Thr Asn Trp Tyr Arg Gly;

and derivatives, analogs, homologs, fragments, salts and mixtures thereof.

In various other preferred embodiments, the peptide or peptide analog has an acetylated amino terminus and/or an amidated carboxy terminus. Examples of such peptide or peptide analogs include:

(SEQ ID NO:1)
$H_2N$--Met-Phe-Leu-Lys-Ala-Val-Val-Leu-Thr-Val-Ala-Leu-Val-Ala-Ile-Tbr-Gly-Thr-Gln-Ala-Glu-Val-Thr-Ser-Asp-Gln-Val-Ala-Asn-Val--$CONH_2$;

(SEQ ID NO:16)
$H_2N$--Thr Pro Gly Asp Phe His Tyr Leu Asp Gly Ala Ser Val Asn Tyr Thr Asn Trp Tyr Pro Gly--$CONH_2$;

(SEQ ID NO:17)
$H_2N$--Ser Pro Gly Asp Phe Arg Tyr Ser Asp Gly Thr Pro Val Asn Tyr Thr Asn Trp Tyr Arg Gly--$CONH_2$;

and derivatives, analogs, homologs, fragments, salts and mixtures thereof.

By "derived from" is meant having an amino acid sequence identical or substantially identical to the sequence of, as used herein, a surfactant-associated protein. By "substantially identical to" is meant having an amino acid sequence that differs only by conservative amino acid substitutions or by non-conservative amino acid substitutions, deletions, or insertions located at positions that do not destroy the biological activity of the peptide.

It is possible to design any number of peptide analogs, having different amino acid sequences, provided that the local charge distribution (and overall net charge) and secondary structure, and hence the biological activity is maintained. Such peptide analogs will generally differ from the native protein sequences by conservative amino acid substitutions (e.g., substitution of Leu for Val, or Arg for Lys, etc.) well known to those skilled in the art of biochemistry.

The peptides, once designed, can be synthesized by any of a number of established procedures, including, e.g., the expression of a recombinant DNA encoding that peptide in an appropriate host cell. Alternatively, these peptides can be produced by the established procedure of solid phase peptide synthesis. Briefly, this procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent. The peptides so synthesized are then labeled with a reagent that enables the monitoring of the peptide after its administration to a patient. Finally, the SP-A and SP-D may be purified from natural sources including, but not limited to, human.

Preferably the synthesized peptide substantially corresponds to the amino acid sequence of an antioxidant or antimicrobial lung surfactant peptide, or to a portion of an antioxidant or antimicrobial lung surfactant peptide which maps to antioxidant or antimicrobial activity. As used herein, the term "substantially corresponds" means a peptide amino acid sequence having approximately 70% homology in amino acid sequence to an antioxidant or antimicrobial lung surfactant peptide.

The term "chemical derivative" is meant to include any peptide derived from a peptide of the present invention wherein one or more amino acids have been chemically derivatized by reaction of one or more functional side groups of the amino acid residues present in the peptide. Thus, a "chemical derivative" as used herein is a peptide that is derived from the peptides identified herein by one or more chemical steps. Examples of derivatized molecules include molecules where free amino groups have been derivatized to form amine hydrochlorides, p-toluene sulfonyl groups, carbobenzoxy groups, t-butyloxycarbonyl groups, thiourethane-type derivatives, trifluroroacetyl groups, chioroacetyl groups or formyl groups. Free carboxyl groups may be derivatized to form salts, methyl and ethyl esters or other types of esters or hydrazides.

Free hydroxyl groups may be derivatized to form O-acyl or O-alkyl derivatives. The imidazole nitrogen of histidine may be derivatized to form N-imbenzylhistidine. Also included as chemical derivatives are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "fragment" refers to any subject peptide having an amino acid sequence shorter than that of a peptide provided herein as any of SEQ ID NOS: 1-17 wherein the fragment retains antioxidant or antimicrobial properties of the subject peptides. The peptides of the present invention, homologs and analogs thereof may be synthesized by a number of known techniques. For example, the peptides may be prepared using the solid-phase synthetic technique or other peptide synthesis techniques well known to those skilled in the art. The peptides of the present invention might also be prepared by chemical or enzymatic cleavage from larger portions of the lung surfactant protein compound or from the entire lung surfactant molecule.

Additionally, the peptides of the present invention may also be prepared by recombinant DNA techniques. For most of the amino acids used to build proteins, more than one coding nucleotide triplet (codon) can code for a particular amino acid residue. This property of the genetic code is known as redundancy. Therefore, a number of different nucleotide sequences may code for a particular subject eating suppressant peptide. The present invention also contemplates a deoxyribonucleic acid (DNA) molecule or segment that defines a gene coding for, i.e., capable of expressing, a subject polypeptide or a subject chimeric polypeptide from which a polypeptide of the present invention may be enzymatically or chemically cleaved.

DNA molecules that encode the subject peptides can be synthesized by chemical techniques, for example, the phosphotriester method of Matteuccie et al., *Chem. Soc.* 103: 3185 (1981). Using a chemical DNA synthesis technique, desired modifications in the peptide sequence can be made by making substitutions for bases that code for the native amino acid sequence. Ribonucleic acid equivalents of the above-described DNA molecules may also be used.

A nucleic acid molecule comprising a vector capable of replication and expression of a DNA molecule defining coding sequence for a subject polypeptide or subject chimeric polypeptide is also contemplated.

The peptides of the present invention are preferably chemically synthesized by the Merrifield solid phase technique. In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the subject peptides include inorganic bases such as sodium hydroxide, ammonium hydroxide, potassium hydroxide and the like; and organic bases such as mono-, di-and tri-alkyl amines (e.g., triethyl amine, diisopropyl amine, methyl amine, dimethyl amine and the like) and optionally substituted ethanolamines (e.g. ethanolamine, diethanolamine and the like).

The peptides of the present invention may be synthesized using an automatic solid phase peptide synthesizer.

Antioxidants or antimicrobial lung surfactant protein compounds, which include lung surfactant protein compounds and derivatives, analogs, homologs, salts and fragments thereof which have antioxidant or antimicrobial properties, may be used therapeutically. Preferred therapeutic antioxidant or antimicrobial lung surfactant protein compounds are lipid oxidation inhibiting or antimicrobial peptides.

It is understood that the present invention is not limited by any particular theory or proposed mechanism to explain its effectiveness in an end-use application.

Therapies

Lung injury, such as pneumonia, is a disease state characterized by the development or persistence of pulmonary infiltrates, reduced lung compliance and reduced gas exchange. The identification of those patients who are in need of treatment for acute lung injury is well within the ability and knowledge of one of ordinary skill in the art. For example, individuals who are either suffering from clinically significant acute lung injury (ALI) or who are at risk of developing clinically significant acute lung injury are patients in need of treatment. A clinician of ordinary skill in the art can readily determine, by the use of clinical tests, physical examination and medical/family history, if an individual is a patient in need of treatment for acute lung injury.

Antioxidant and antimicrobial lung surfactant protein compounds in accordance with the present invention may be used in treating acute lung injury, including adult respiratory distress syndrome and hyperoxic lung injury. In one embodiment a patient with adult respiratory distress syndrome or hyperoxic lung injury is treated with SP-A and/or SP-D, or a peptide which corresponds to the portions of SP-A and/or SP-D which map to antioxidant or antimicrobial activity. In another embodiment, the patient is treated with a peptide having an amino acid sequence selected from the group consisting of SEQ ID NOS: 1-17, preferably SEQ ID NOS: 1, 4-6, 9-15 and 17. Generally the patient is treated with an amount of antioxidant or antimicrobial lung surfactant protein compound that is effective, upon single or multiple dose administration to the patient, in providing relief of symptoms associated with acute lung injury.

An effective dose is an amount that is effective in inhibiting the development or persistence of acute lung injury in a patient in need thereof. As such, successful treatment of a patient for acute lung injury is understood to include effectively slowing, interrupting, arresting, or stopping acute lung injury and/or pneumonia and does not necessarily indicate a total elimination of acute lung injury. It is appreciated by those of ordinary skill in the art that successful treatment for ALI can include prophylaxis in preventing ALI.

Peroxidation of surfactant lipids, such as the unsaturated fatty acid portions of surfactant cholesteryl lipids and surfactant phospholipids, is known to cause surfactant dysfunction. The identification of those patients who are in need of inhibition of peroxidation of surfactant lipids is well within the ability and knowledge of one of ordinary skill in the art. For example, those individuals who are in need of treatment for acute lunge injury, as defined above, are also patients who are in need of inhibition of peroxidation of surfactant lipids. A preferred antioxidant or antioxidation amount is an amount sufficient for inhibiting the peroxidation of surfactant lipids in a patient's lung.

As used herein, the term "patient" refers to a warm-blooded animal or mammal which is in need of treatment for a chronic heart disease, atherosclerosis, hypercholesterolemia or which is in need of inhibiting oxidation.

A "therapeutically effective amount" is an amount that is effective, upon single or multiple dose administration to the patient, in providing relief of symptoms associated with acute lung injury and/or pneumonia.

As used herein, "relief of symptoms" refers to decrease in severity over that expected in the absence of treatment and does not necessarily indicate a total elimination or cure of the disease. Relief of symptoms is also intended to include prophylaxis.

In determining the therapeutically effective amount or dose, the effective antioxidant or antimicrobial amount or dose of an antioxidant or antimicrobial lung surfactant protein compound, a number of factors are considered by the attending diagnostician, including, but not limited to: the species of the mammal; its size, age, and general health; the response of the individual patient; the particular compound administered; the mode of administration; the bioavailability characteristics of the preparation administered; the dose regimen selected; the use of concomitant medication; and other relevant circumstances.

A therapeutically effective amount will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

Antioxidant and antimicrobial peptides in accordance with the invention may also be used in the treatment of atherosclerosis and systemic infections. Atherosclerosis is a disease state characterized by the development and growth of atherosclerotic lesions or plaque. Peroxidation of LDL lipid, such as the unsaturated fatty acid portions of LDL cholesteryl esters and phospholipids, is known to facilitate the deposition of cholesterol in macrophages which subsequently are deposited in the vessel wall and are transformed into foam cells. It is appreciated by those of ordinary skill in the art that successful treatment for atherosclerosis can include prophylaxis in preventing atherosclerotic lesion or plaque formation. Systemic infections comprise disease states characterized by the infection in the blood stream or major body cavities or organs. It is appreciated by those of ordinary skill in the art that successful treatment for systemic infections can include prophylaxis in preventing sepsis. Local infections, such as skin, wound, eye, mucosal, ear, or perineal infections may also be treated with topical preparations containing surfactant proteins or peptides.

In effecting treatment of a patient, an antioxidant or antimicrobial lung surfactant protein compound, or any derivative, analog, homolog, salt, fragment or mixture thereof, can be administered in any form or mode which makes the compound bioavailable in effective amounts. Suitable modes of administration include oral, topical, rectal enteral or parenteral administration. Parenteral administration may include intratracheal or inhalant aerosol administration, transdermal administration, subcutaneous injection, intravenous injection, intraperitoneal injection, intramuscular injection, intrasternal injection, intrathecal injection, intraventricular and intracerebroventricular injection and infusion techniques. Intratracheal administration or inhalation of aerosolized compositions are generally preferred. One skilled in the art of preparing formulations can readily select the proper form and mode of administration depending upon the relevant circumstances.

An antioxidant or antimicrobial lung surfactant protein compound, derivative, analog, homolog, fragment, salt or mixtures thereof can be administered in the form of pharmaceutical compositions or medicaments which are made by combining an antioxidant or antimicrobial lung surfactant protein compound, or any derivative, analog, homolog, salt, fragment or mixture thereof, with pharmaceutically acceptable carriers or excipients, the proportion and nature of which are determined by the chosen route of administration, and standard pharmaceutical practice. The term “pharmaceutically acceptable” refers to a molecular entity or composition that does not produce an allergic or similar unwanted reaction when administered to animals or humans. Preferred carriers include natural and synthetic surfactant phospholipids.

The pharmaceutically acceptable carriers used in conjunction with the peptides of the present invention vary according to the mode of administration. For example, the compositions may be formulated in any suitable carrier for oral liquid formulation such as suspensions, elixirs and solutions. Compositions for liquid oral dosage include any of the usual pharmaceutical media such as, for example, water, oils, alcohols, flavoring agents, preservatives, coloring agents and the like. In the case of oral solid preparations (powder capsules and tablets) carriers such as starches, sugars, diluents, granulating agents, lubricants, binders, disintegrating agents and the like may be used. In addition, carriers such as liposomes, microemulsions and self-emulsifiable glasses may be used.

The compositions of the present invention may also be formulated for intravenous administration. In this instance, the peptides are admixed with sterile water and saline or other pharmaceutically acceptable carrier.

The pharmaceutical compositions or medicaments are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, an antioxidant or antimicrobial lung surfactant protein compound, derivative, salt or fragment thereof may be incorporated with excipients and used in the form of tablets, troches, capsules, elixirs, suspensions, syrups, wafers, chewing gums and the like. These preparations should contain at least about 4% of an antioxidant or antimicrobial lung surfactant protein compound, derivative, salt or fragment thereof the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, an antioxidant or antimicrobial lung surfactant protein compound, derivative, analog, homolog, fragment, salt or mixtures thereof may be incorporated into a solution or suspension. These preparations should contain at least about 0.1% of a compound of the invention, but may be varied to be between about 0.1 and about 50% of the weight thereof. The amount of the active ingredient present in such compositions is such that a suitable dosage will be obtained.

When administered intravenously, the peptide compositions may be combined with other ingredients, such as carriers and/or adjuvants. The peptide can also be covalently attached to a protein carrier, such as albumin, so as to minimize clearing of the peptides. There are no limitations on the nature of the other ingredients, except that they must be pharmaceutically acceptable, efficacious for their intended administration and cannot degrade the activity of the active ingredients of the compositions. The peptide compositions of the invention may also be impregnated into transdermal patches or contained in subcutaneous inserts, preferably in a liquid or semi-liquid form that patch or insert time releases therapeutically effective amounts of one or more of the subject peptides.

The pharmaceutical forms suitable for administration intravenously or into the airways include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject peptides is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

The solutions or suspensions may also include one or more of the following adjuvants depending on the solubility and other properties of an antioxidant or antimicrobial lung surfactant protein compound, derivative, salt or fragment thereof: sterile diluents such as water for injection, saline solution, fixed oils, polyethylene glycols, glycerine, propylene glycol or other synthetic solvents; antibacterial agents such as benzyl alcohol or methyl paraben; antioxidants or antimicrobials such as ascorbic acid or sodium bisulfite; chelating agents such as ethylene diaminetetraacetic acid; buffers such as acetates, citrates or phosphates and agents for the adjustment of toxicity such as sodium chloride or dextrose.

The parenteral preparation can be enclosed in ampules, disposable syringes or multiple dose vials made of glass or plastic.

The pharmacological composition will preferably comprise one or more antioxidant or antimicrobial lung surfactant protein compounds thereof along with a pharmaceutically acceptable carrier, fillers or excipients. The administering step may comprise administering a pharmacological composition comprising an antioxidant or antimicrobial lung surfactant protein compound, derivative, salt or fragment thereof along with pharmaceutically acceptable carrier, fillers or excipients.

The methods may be by oral administration of the composition or a pharmaceutically acceptable salt or derivative thereof into said mammal. The methods according to the present invention preferable allows the administration of the antioxidant or antimicrobial molecule is administered in a unitary dose of from about 1 to about 1000 mg. A unitary dose is generally administered from about 1 to about 3 times a day.

The administering step may comprise parenteral administration of the antioxidant or antimicrobial compound or a pharmaceutically acceptable salt or derivative thereof into said mammal. This administration may be by transdermal administration, subcutaneous injection, intravenous injection, intraperitoneal injection, intramuscular injection, intrasternal injection, intrathecal injection, intracerebroventricular injection and infusion techniques. Preferred techniques include intratracheal administration and administration by inhalation of aerosolized compositions, such as with a nebulized or metered dose inhaler.

Methods in accordance with the present invention also include methods which comprise administering antioxidant or antimicrobial compounds or a pharmaceutically acceptable salt or derivative thereof along with a lipophilic compound, such as a lipophilic solvent or carrier. The lipophilic solvent or carrier may be an organic solvent, phosphatidylcholine, cholesterol, or surfactant phospholipids.

The pharmaceutical compositions of the present invention can be formulated for the inhaled, intratracheal, oral, sublingual, subcutaneous, intravenous, transdermic or rectal administrations in dosage units and in admixture with pharmaceutical excipients or vehicles. Convenient dosage forms include, among those for oral administration, tablets, powders, granulates, and, among those for parenteral administration, solutions especially for transdermal administration, subcutaneous injection, intravenous injection, intraperitoneal injection, intramuscular injection, intrasternal injection, intrathecal injection and infusion techniques.

The dosage can vary widely as a function of the age, weight and state of health of the patient, the nature and the severity of the ailment, as well as of the administration route. These doses can naturally be adjusted for each patient according to the results observed and the blood analyses previously carried out.

Food Preservatives

The antioxidant or antimicrobial lung surfactant protein compounds of the present invention may be made into edible nonionic water-or lipid-soluble additives that are effective antioxidants and/or antimicrobials in food products or ingredients of foods without imparting undesirable flavors, aromas, and precipitates.

Oxidation of fats, vegetable oils, carotenoids and their biologically active derivatives, Vitamin A, and of essential oils and other flavorings results in degradation of their quality, and is deleterious to foodstuffs containing these products. Bacterial contamination, colonization and/or proliferation in food products and ingredients easily occurs in various environments.

The art shows many methods of inhibiting lipid oxidation or microbial proliferation by adding fat-soluble antioxidants or by adding antimicrobials to a substrate. The art does not show the oxidation or microbial stabilization of fats, oils, foods and ingredients of foods employing lung surfactant protein compounds and active derivatives and fragments in a form effective for such purpose.

Methods of preventing oxidation in a lipid-containing food and/or preventing microbial contamination, colonization, persistence or proliferation in a food comprise incorporating in the food an oxidation-inhibiting amount or antimicrobial amount of one or more lung surfactant protein compounds, derivatives, analogs, homologs, fragments, salts or mixtures thereof to protect the food from oxidation or microbial contamination. An oxidation-inhibiting or antimicrobial amount is an amount sufficient to inhibit lipid oxidation or inhibit microbial growth.

The food composition may further comprise carriers, fillers, and excipients. Preferably, the lung surfactant protein compound makes up about 0.01% to about 10% of the final weight of the food product. More preferably, the lung surfactant protein compound makes up from about 0.02% to about 5% of the final weight of the food product.

Further, a fat, oil, fatty food or food ingredient substrate stabilized against oxidation with such composition, such a stabilized substrate wherein the substrate includes a carotenoid, and a method of stabilizing a fat, oil, food, or food ingredient substrate which includes the step of introducing into the substrate such a composition as set forth in the foregoing, and such a method wherein the substrate includes a carotenoid.

Pharmaceutical Compositions

The compositions of the present invention may also be used as a method of preventing oxidation and/or bacterial proliferation in lipid-containing pharmaceuticals. This embodiment involves incorporating in the pharmaceutical an oxidation-inhibiting or antimicrobial amount of one or more lung surfactant protein compounds, or derivative, analog, homolog, fragment, salt or mixture thereof.

The composition may further include carriers, fillers, and excipients. Preferably, the lung surfactant protein compounds makes up about 0.01% to about 25% of the final weight of the pharmaceutical product. More preferably, the lung surfactant protein compounds makes up from about 0.05% to about 10% of the final weight of the pharmaceutical product.

Cosmetic or Dermatological Preparations

In one embodiment, the present invention provides methods of preventing oxidation in a lipid-containing cosmetic or dermatological composition by incorporating, in a suitable vehicle containing cosmetic or dermatological composition, an oxidation-inhibiting amount of one or more antioxidant lung surfactant protein compound, derivative, analog, homolog, fragment, salt or mixtures thereof.

In another embodiment, the present invention provides methods of preventing microbial proliferation in a cosmetic or dermatological composition by incorporating, in a suitable vehicle containing cosmetic or dermatological composition, an antimicrobial amount of one or more antimicrobial lung surfactant protein compounds, or derivatives, analogs, homologs, fragments, salts or mixtures thereof.

The composition may further comprise carriers, fillers, and excipients. Preferably, the antioxidant or antimicrobial lung surfactant protein compound is present at a concentration between about 0.005% and about 25% by weight with respect to the total weight of the composition. More preferably, the lung surfactant protein compound is present at a concentration between about 0.05% and about 10% by weight with respect to the total weight of the composition.

In another embodiment, the present invention relates to a new antioxidant or antimicrobial system based on one or more lung surfactant protein compounds, derivative, analog, homolog, fragment, salt or mixtures thereof for use as an antioxidant or antimicrobial system in compositions based on an oleaginous material containing such a system and, principally, cosmetic compositions.

This embodiment generally provides for a cosmetic or dermatological composition containing, in a suitable vehicle, an oxidation-inhibiting amount or antimicrobial amount of a lung surfactant protein compound, derivative, analog, homolog, fragment, salt or mixtures thereof.

The cosmetic or dermatological composition may be in the form of a suspension or dispersion in a solvent or a fatty substance, or in the form of an emulsion, or in the form of an ointment, a gel, a solid stick, or an aerosol foam.

The cosmetic or dermatological composition may additionally contain one or more cosmetic adjuvants such as lower alcohols, polyols, esters of, fatty acids, oils, and waxes, solvents, silicones, thickeners, emollients, UV-A, UV-B and broad band sunscreens, antifoam agents, hydrating agents, perfumes, stabilizers, surfactants, fillers, sequestrants, anionic, cationic, nonionic and amphoteric polymers and mixtures thereof, propellants, alkalifying and acidifying agents, dyes and metal oxide pigments.

Preferably, the lung surfactant protein compound is present at a concentration between about 0.001% and about 25% by weight with respect to the total weight of the composition. More preferably, the lung surfactant protein compound is present at a concentration between about 0.005% and about 15% by weight with respect to the total weight of the composition.

In another embodiment, the present invention relates to an antioxidant or antimicrobial cosmetic system based on lung surfactant protein compounds or at least one of its derivatives, salts or fragments thereof which contains either at least one basic agent or includes at least one tocopherol or a derivative thereof. Preferably the system contains from about 0.5 to about 20 weight percent of a tocopherol or derivative thereof, about 0.5 to about 50 weight percent of a basic agent and about 0.5 to about 90 weight percent of lung surfactant protein compounds and derivatives, salts and fragments thereof. This system is employed in cosmetic or pharmaceutical compositions.

The present invention thus relates to a new antioxidant or antimicrobial system based on at least one basic agent characterized by the fact that the system also includes at least one tocopherol or tocopherol derivative and lung surfactant protein compound, derivative, analog, homolog, fragment, salt or mixtures thereof.

Sodium hydroxide, triethanolamine, basic amino acid may, for example, be used as the basic agent. By basic amino acid is meant a natural basic amino acid such as, for example, lysine, arginine and histidine, their isomeric or racemic forms, as well as synthetic basic amino acids and derivatives of natural amino acids. Preferably, in accordance with the present invention, lysine or arginine is employed.

By the expression "tocopherol" there is meant not only alpha-tocopherol but also beta, gamma or delta tocopherol as well as their mixtures. Among the tocopherol derivatives mention can be made of the esters of tocopherol such as tocopherol acetate and tocopherol nicotinate.

According to the invention, the antioxidant or antimicrobial system comprises, by weight:

from about 0.5 to about 40 percent of a tocopherol or a tocopherol derivative, from about 0.5 to about 50 percent of a basic amino acid, and from about 0.5 to about 90 percent of lung surfactant protein compounds or derivatives, salts or fragments thereof.

The preferred ratio between the concentration of the basic amino acid and the concentration of the tocopherol ranges from about 1:1 to about 1:20.

The compositions according to the invention are provided in the form of oily solutions, water-in-oil or oil-in-water emulsions, optionally anhydrous products, lotions or even microdispersions or ionic or nonionic lipid vesicles. They constitute principally milks for the care of the skin, creams (face creams, hand creams, body creams, sunscreen creams, make-up remover creams, foundation creams), foundation fluids, make-up remover milks, sunscreen milks, bath oils, lipsticks, eyelid make-up, deodorant sticks, etc.

For topical application, the pharmaceutical compositions according to the invention comprise vehicles and ingredients necessary to provide, for example, the composition in the form of ointments, creams, milks, pomades and oily solutions.

According to a preferred embodiment, the cosmetic or dermopharmaceutical compositions are provided in forms intended to be topically applied and, in particular, creams intended for the protection of the lipids of the skin against oxidation.

In the compositions according to the invention, the antioxidant or antimicrobial system is generally present in the composition at a level sufficient to provide, by weight of the total composition:

tocopherol or derivative thereof from about 0.05 to about 2%;

basic agent from about 0.05 to about 5%; and lung surfactant protein compounds from about 0.05 to about 8%.

The compositions of the invention can also contain active compounds or ingredients conventionally employed in compositions mentioned above, such as surface active agents, dyes, perfumes, astringent products, ultraviolet absorbing products, organic solvents, water, etc. These compositions are prepared in accordance with conventional methods.

The compositions of the invention may also contain, in the aqueous phase, various complementary additives such as preserving agents, sequestering agents, gelling agents and the like. The compositions of the invention may also contain, in the lipid phase, various complementary additives such as oils, waxes or gums having, for example, emollient or lubricating properties. The compositions are most often provided in milk, cream or gel form, other modes of presentation not being excluded.

In another embodiment, the present invention provides a process for the preparation of the compositions described above, comprising:

(i) mixing (a) a fatty phase, comprising the lipophilic surfactant, the hydrophilic surfactant, and the fatty acid and (b) an aqueous phase comprising the basic agent and the cosmetically or dermatologically active lung surfactant protein compound by stirring to obtain a mixture; and (ii) homogenizing the mixture by subjecting the mixture to cavitation.

For cosmetic applications, the compositions of the invention may, moreover, be advantageously used in combination with other compounds displaying retinoid-type activity, with the D vitamins or derivatives thereof, with corticosteroids, with anti-free radical agents, with alpha-hydroxy or alpha-keto acids or derivatives thereof, or alternatively with ion channel blockers, all of these different active agents.

The present invention therefore also features cosmetic compositions comprising a carrier that is cosmetically acceptable and suitable for a topical application and lung surfactant protein compounds. Such cosmetic compositions are advantageously presented in the form of a cream, a milk, a lotion, a gel, microspheres or nanospheres or lipid or polymeric vesicles, a soap or a shampoo.

The concentration of the lung surfactant protein compound, derivative, analog, homolog, salt, fragment or mixture thereof in the cosmetic compositions according to the invention advantageously ranges from about 0.001% to about 30%, by weight of total composition.

The medicinal and cosmetic compositions according to the invention may, in addition, contain inert or even pharmacodynamically or cosmetically active additives or combinations of these additives, and, especially: wetting agents; depigmenting agents such as hydroquinone, azelaic acid, caffeic acid or kojic acid; emollients; moisturizing agents such as glycerol, PEG 400, thiamorpholinone and its derivatives or alternatively urea; antiseborrhoeic or antiacne agents such as S-carboxymethylcysteine, S-benzylcysteamine, salts or derivatives thereof, benzoyl peroxide; antibiotics such as erythromycin and esters thereof, neomycin, clindamycin and esters thereof, tetracyclines; antifungal agents such as ketoconazole or 4,5-polymethylene-3-isothiazolidones; agents promoting hair regrowth, such as Minoxidil (2,4-diamino-6-piperidinopyrimidine 3-oxide) and derivatives thereof, Diazoxide (7-chloro-3-methyl-1,2,4-benzothiadiazime-1,1-dioxide) and Phenytoin (5,4-diphenyl-2,4-imidazolidinedione); non-steroidal anti-inflammatory agents; carotenoids and especially beta-carotene; anti-psoriatic agents such as anthralin and derivatives thereof; and, lastly, 5,8,11,14-eicosatetraynoic and 5,8,11-eicosatrynoic acids and esters and amides thereof.

The compositions according to the invention may also contain taste- or flavor-enhancing agents, preservatives such as parahydroxybenzoic acid esters, stabilizing agents, moisture regulating agents, pH regulating agents, osmotic pressure modifying agents, emulsifying agents, UV-A and UV-B screening agents, antioxidants and antimicrobials such as alpha-tocopherol, butylated hydroxyanisole or butylated hydroxytoluene.

The following examples illustrate and explain the present invention but should not be taken as limiting the present invention in any regard.

EXAMPLES

Methods

Purification and modification of surfactant proteins-antioxidant properties

Native SP-A and SP-D were isolated from the alveolar wash of rats which had been pretreated with intratracheal silica to enhance the collectin yield, in accordance with the method of Dethloff et al., *Biochem. J.* 233:111-118 (1986). After centrifugation, rat SP-D was purified by maltose-Sepharose affinity chromatography of the supernatant and rat SP-A was purified from the pellet by NaBr flotation, butanol extraction and mannose-Sepharose affinity chromatography, in accordance with the method of McCormack et al., *J. Biol. Chem.* 272:27971-27979 (1997). Mouse SP-D was used interchangeably with rat SP-D. All proteins were extensively dialyzed to remove residual EDTA. For some experiments, rat SP-A and rat SP-D were alkylated by incubation with 0.5 M iodoacetamide at 37° C. in the dark for 1 hr and then extensively dialyzed. The wild type and mutant recombinant SP-A, SP-D and MBP used in this study were synthesized using baculovirus vectors and purified by carbohydrate-Sepharose affinity chromatography, as previously described in McCormack et al., *J. Biol. Chem.* 272:27971-27979 (1997); McCormack et al., *Biochemistry* 36:13963-13971 (1997); and McCormack et al., *J. Biol. Chem.* 274:3173-3183 (1999).

Lipid preparations

Substrates for lipid oxidation included mixtures of natural and synthetic glycerophospholipids that are found in pulmonary surfactant and human LDL. The surfactant lipid mix, composed of egg phosphatidylcholine, dipalmitoylphosphatidylcholine, cholesterol and 1-oleoyl-2-linoleoyl-sn-glycero-3-phosphocholine (1:1:0.15:0.15, w/w, respectively) (Avanti Polar Lipids) in chloroform, was dried to a film under nitrogen. Following hydration in PBS or 0.15 M NaCl for 30 min, multilamellar vesicles were generated by vigorous vortexing for 5 minutes. LDL were isolated from the plasma of normal blood donors by density gradient ultracentrifugation (density=1.019-1.063 g/ml) as previously described in Qin et al., *Am. J. Physiol.* 274(5 Pt 2): H1836-1840 (1998), and stored in saline-EDTA. Just prior to use, EDTA was removed by dialysis against PBS, and the concentration of LDL was determined by Lowry assay (in milligrams of LDL-associated protein).

Assessment of lipid oxidation

Stock solutions of 10 mM $CuSO_4$ were freshly prepared daily. Reaction mixtures containing 1 mg/mi surfactant lipids or 150 μg/ml LDL were incubated with 10 μM $CuSO_4$ for 24 hours or 4 hours, respectively, in the presence of putative oxidation inhibitors or controls at 37° C. in a shaking water bath in accordance with the method of Gelvan et al., *Biochim. Biophys. Acta* 1035(3):353-360 (1990). Control reactions which included LDL only, 10 μM $CuSO_4$ or protein controls of bovine serum albumin (BSA), rat IgG, recombinant MBP, rat serum and human complement C1q were performed concurrently with experimental samples. Thiobarbituric acid-reactive substances (TBARS) were measured using a method adapted from Gelvan et al., *Biochim. Biophys. Acta* 1035(3):353-360 (1990). Samples and 0-10 μM 1,1,3,3-methylmalondialdehyde standards were developed by addition of a solution composed of 0.375% thiobarbituric acid, 15% trichloroacetic acid, and 0.25N HCl at a volume ratio of 1:2, sample: developer. Following incubation at 95° C. for 30 minutes and centrifugation at 14,000 rpm for 15 minutes, an aliquot was read at 540 nM in a spectrophotometer. For continuous assessment of lipid oxidation, the accumulation of conjugated dienes during LDL oxidation was monitored spectrophotometrically in accordance with the method of Esterbauer et al., *Free Rad. Med. Biol.* 13, 341-390 (1992). Mixtures of 150 μg/ml LDL, 10 μM copper, and various amounts of surfactant proteins or control proteins were placed in quartz cuvettes and allowed to oxidize at room temperature over 335 minutes. Conjugated diene formation was assessed by measuring absorbance at 234 nm in a spectrophotometer.

Detection of Protein Oxidation by Western Blot Analysis

Proteins were analyzed for carbonyl modification of amino acid side groups that occur during lipid oxidation, as described in Levine et al., *Methods Enzymol.* 186, 464-478 (1990). Briefly, proteins that were included in reactions mixtures with LDL and 10 μM copper were derivatized to 2,4-dinitrophenylhydrazones (DNP-hydrazones) by reaction with 2,4-dinitrophenylhydrazine (DNPH), size fractionated by 8-16% SDS-PAGE under reducing conditions and electrophorectically transferred to nitrocellulose membranes (Oxyblot, Intergen). The membrane was sequentially incubated with a rabbit anti-DNP IgG and a horseradish peroxidase-conjugated goat anti-rabbit IgG. Blots were developed by HRP-dependent oxidation of a chemiluminescent substrate, and visualized using autoradiography.

Cell oxidation experiments

A murine macrophage cell line (RAW 264.7) was adhered to 24-well plates ($2\times10^4$ cells/well) in Ham's F12 media containing 10% FBS overnight at 37° C. in a 10% $CO_2$ atmosphere. After washing, the cells were exposed to 40 μM tert-butyl hydroperoxide (t-BOOH) in serum free Ham's F12 for 24 hrs in the presence of various concentrations of the surfactant proteins. Viability was assessed for exclusion of the vital dye Trypan Blue.

Results

Effects of pulmonary collectins on lipid oxidation

The ability of SP-A and SP-D to inhibit the copper-induced oxidation of a mixture of saturated and unsaturated lipids was assessed by measuring the accumulation of thiobarbituric reactive substances (TBARS) during a 24 hr incubation at 37° C., as illustrated by FIG. 1*a*. Panel a sets forth data obtained when surfactant lipids were incubated with 10 μM $Cu^{2+}$ in the presence of the indicated concentrations of surfactant proteins SP-A or SP-D, while panel b sets forth data obtained when LDL particles were incubated with 10 μM $Cu^{2+}$ in the presence of the indicated concentrations of surfactant proteins SP-A or SP-D.

Native SP-A isolated from rat lungs inhibited oxidation of surfactant lipids in a dose-dependent fashion that was half maximal at a concentration of 5.07 μg/ml ($I.C._{50}$=8.4 nM, assuming rat SP-A M.W.=600,000 kDa) and complete at 10 μg/ml. Native SP-D also inhibited copper-induced surfactant lipids oxidation in a dose-dependent manner with maximal protection observed at doses equal to or greater than 0.5 ug/ml. The $I.C._{50}$ for protection by SP-D was 0.11 μg/ml ($I.C._{50}$=0.2 nM, assuming rat SP-D M.W.=500,000), or approximately 35-fold lower than SP-A, and 100-fold lower than the antioxidant serum lipoprotein ApoAIV ($I.C._{50}$=50 nM). The inhibitory concentrations for both lung proteins were well below their physiologic ELF levels, estimated to be 300-1800 μg/ml for SP-A and 36-216 μg/ml for SP-D. Alkylation of SP-A and SP-D with iodoacetamide completely blocked the antioxidant effects of the proteins but neither the presaturation of SP-A with 70 uM copper, as indicated in Table 1, below, or the addition of 2 mM $Ca^{2+}$ (not shown) had a significant effect on the activity. There was no protection from oxidation by control proteins albumin, rat serum or the structurally similar molecule, C1q (the first component of complement), at concentrations of 50 μg/ml, as indicated in Table 1, below. A rat serum concentration of 500 μg/ml was required to achieve the same level of inhibition of oxidation that occurred with about 5.0 μg/ml SP-A or 0. 1-0.2 μg/ml SP-D. These data indicate that the two hydrophilic surfactant proteins, SP-A and SP-D, protect surfactant lipids from copper-induced oxidation at physiologically relevant concentrations.

TABLE 1

TBARS from copper-induced oxidation of surfactant lipids or LDL

| Reaction mixture | Surfactant lipids Malondialdehyde (μM) | LDL Malondialdehyde (μM) |
|---|---|---|
| Lipid* only | 0.35 ± 0.03 | 0.01 ± 0.01 |
| Lipid + $Cu^{2+}$ | 1.21 ± 0.10 | 4.15 ± 0.08 |
| Lipid + $Cu^{2+}$ + 10 μg/ml SP-A | 0.23 ± 0.01 | 0.0 ± 0.0 |
| Lipid + $Cu^{2+}$ + 10 μg/ml $Cu^{2+}$ presat SP-A | 0.13 ± 0.03 | ND |
| Lipid + $Cu^{2+}$ + 1 μg/ml SP-D | 0.27 ± 0.07 | 0.0 ± 0.0 |
| Lipid + $Cu^{2+}$ + 20 μg/ml rMBP | ND | 4.47 ± 0.02 |
| Lipid + $Cu^{2+}$ + 50 μg/ml BSA | 1.14 ± 0.11 | 3.88 ± 0.22 |
| Lipid + $Cu^{2+}$ + 50 μg/ml rat serum | 1.69 ± 0.15 | 4.06 ± 0.08 |
| Lipid + $Cu^{2+}$ + 500 μg/ml rat serum | 0.509 ± 0.06 | 3.03 ± 0.96 |
| Lipid + $Cu^{2+}$ + 50 μg/ml Clq | 1.15 ± 0.07 | 4.16 ± 0.05 |
| Lipid + $Cu^{2+}$ + 50 μg/ml IgG | ND | 4.15 ± 0.21 |
| Lipid + $Cu^{2+}$ + 10 μg/ml alkylated SP-A | 1.36 ± 0.18 | ND |
| Lipid + $Cu^{2+}$ + 50 μg/ml alkylated SP-A | ND | 4.21 ± 0.25 |
| Lipid + $Cu^{2+}$ + 10 μg/ml alkylated SP-D | ND | 3.92 ± 0.14 |

TABLE 1-continued

| TBARS from copper-induced oxidation of surfactant lipids or LDL | | |
|---|---|---|
| Reaction mixture | Surfactant lipids Malondialdehyde (μM) | LDL Malondialdehyde (μM) |
| Lipid + $Cu^{2+}$ + 20 μg/ml ΔN1-P80, N187S | 0.21 ± 0.18 | 0.01 ± 0.01 |

*Lipid used was surfactant lipids of LDL, as noted in adjacent columns.
Data is mean ± S.E.M., n = 3.
ND = not done
Clq = the first component of complement
MBP = mannose binding protein
ΔN1-P80, N187S = a nonglycosylated neck and CLD construct containing an Asn187Ser mutation Both SP-A and SP-D exhibited very similar antioxidant activity when the lipid components of LDL particles including unsaturated phospholipids, triglycerides, cholesterol and cholesterol esters were used as the substrates for lipid oxidation, as illustrated in FIG. 1*b*. The I.C.$_{50}$ for inhibition of copper-induced oxidation of LDL for SP-A and SP-D were 4.75 μg/ml (7.9 nM) and 0.14 μg/ml (0.3 nM) respectively, and complete inhibition of oxidation occurred at 10 μg/ml and 1 μg/ml, respectively. In contrast, 20 μg/ml of the highly homologous collectin, recombinant rat mannose binding protein A (MBP-A) did not inhibit LDL oxidation, as indicated in Table 1, below. Rat serum, albumin, C1q and IgG had also no effect on LDL lipid oxidation at concentrations of 50 μg/ml, as indicated in Table 1, below. Only 2.5 μg/ml SP-A or 0.05 μg/ml SP-D were required to provide the same level of antioxidant protection as 500 μg/ml of rat serum. In the absence of oxidation inhibitors, the absolute TBARS level following a 4 hour incubation with 10 μM copper was over 3 times greater for LDL than for surfactant lipids, as indicated by Table 1. For this reason, LDL was used as the lipid substrate for kinetic experiments and mutagenesis studies of the collectin antioxidant activities.

Kinetic analysis of c Ilectin antioxidant activity

The temporal relationship between the addition of SP-A or SP-D and the inhibition of LDL oxidation was determined spectrophotometrically by continuously monitoring conjugated diene accumulation associated with exposure to copper, in accordance with the method of Esterbauer et al., *Free Rad. Med. Biol.* 13:341-390 (1992). The assay is based on the oxidation dependent rearrangement of 1,4 pentadienyl double bonds of LDL lipids to 1,3-butadienyl double bonds, which absorb in the ultraviolet range. In the presence of 10 μM copper at room temperature, LDL particles resist oxidation for up to 100 minutes as endogenous antioxidants such as atocopherol are consumed. At that point, the rate of oxidation increases in proportion to the concentration of initiating radicals, reaching a plateau when all unsaturated fatty acids are consumed.

Figure 2:
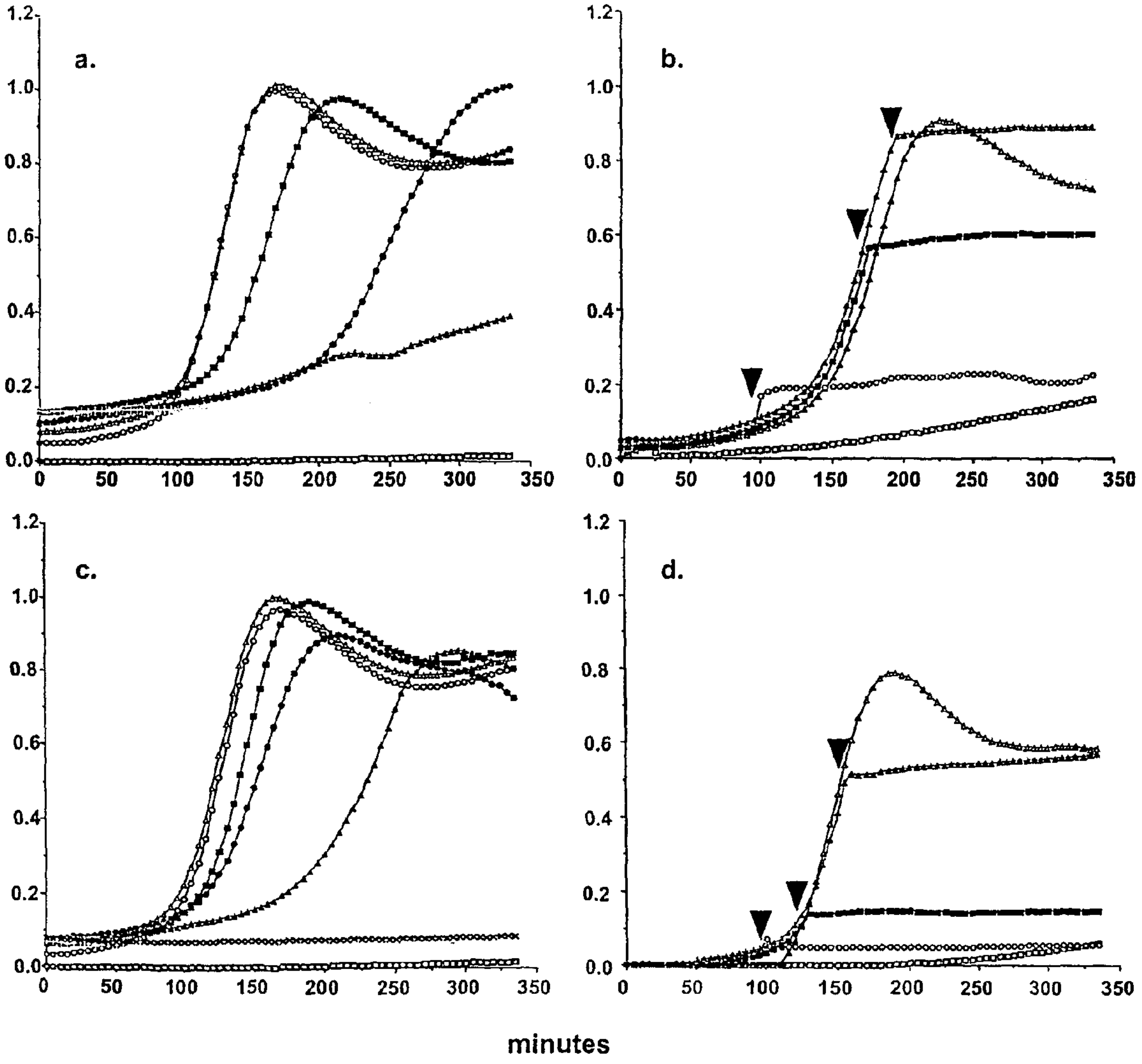
FIG. 2 depicts the continuous analysis of the antioxidant functions of SP-A and SP-D and the inhibition of LDL oxidation as measured by a spectrophotometer.

The data are set forth graphically in FIG. 2. According to FIG. 2, conjugated diene formation during copper-induced LDL oxidation was monitored spectrophotometrically by measuring absorbance at 234 nm. In the absence of copper (open square), only minimal LDL oxidation occurred. Addition of 10 μM copper and (panel a) SP-A at 0 (open triangle), 1.0 (open circle), 2.5 (closed square), 5.0 (closed circle), 7.5 (closed triangle) and 10 μg/ml (cross) or (panel c) SP-D at 0 (open triangle), 0.01 (open circle), 0.05 (closed square), 0.075 (closed circle), 0.1 (closed triangle), 0.5 (x) and 1 μg/ml (cross) at zero time caused a dose-dependent decrease in the slope of propagation curve, with complete inhibition of oxidation at 10 μg/ml SP-A or 0.5 μg/ml SP-D. The effect of collectin addition during the propagation phase of oxidation was also assessed. The addition (arrows) of (panel b) SP-A at 0 μg/ml (open triangle) or 10 μg/ml SP-A at 95 (open circle), 175 (closed square) or 195 (closed triangle) minutes or (panel d) 0 μg/ml SP-D (open triangle) or 1 μg/ml SP-D at 95 (open circle), 125 (closed square), or 155 (closed triangle) minutes arrested lipid oxidation almost immediately.

When SP-A (FIG. 2*a*) or SP-D (FIG. 2*c*) were included at zero time, they blocked the accumulation of conjugated dienes in a dose-dependent manner. With increasing surfactant protein concentrations, the predominant change was a decrease in the slope during the rapid oxidation phase, consistent with inhibition of free radical chain initiation or with free radical chain termination. The concentrations of SP-A and SP-D that prevented conjugated diene formation were very similar to those that were required to block TBARS formation. When fully suppressive concentrations of SP-A (10 μg/ml)(FIG. 2*b*) or SP-D (1 μg/ml) (FIG. 2*c*) were added during the propagation phase of oxidation, conjugated diene formation was completely arrested at the point of addition. These data indicate that SP-A and SP-D directly interfere with lipid oxidation.

Pulmonary collectin domains and mechanisms in prevention of lipid oxidation

Figure 3:
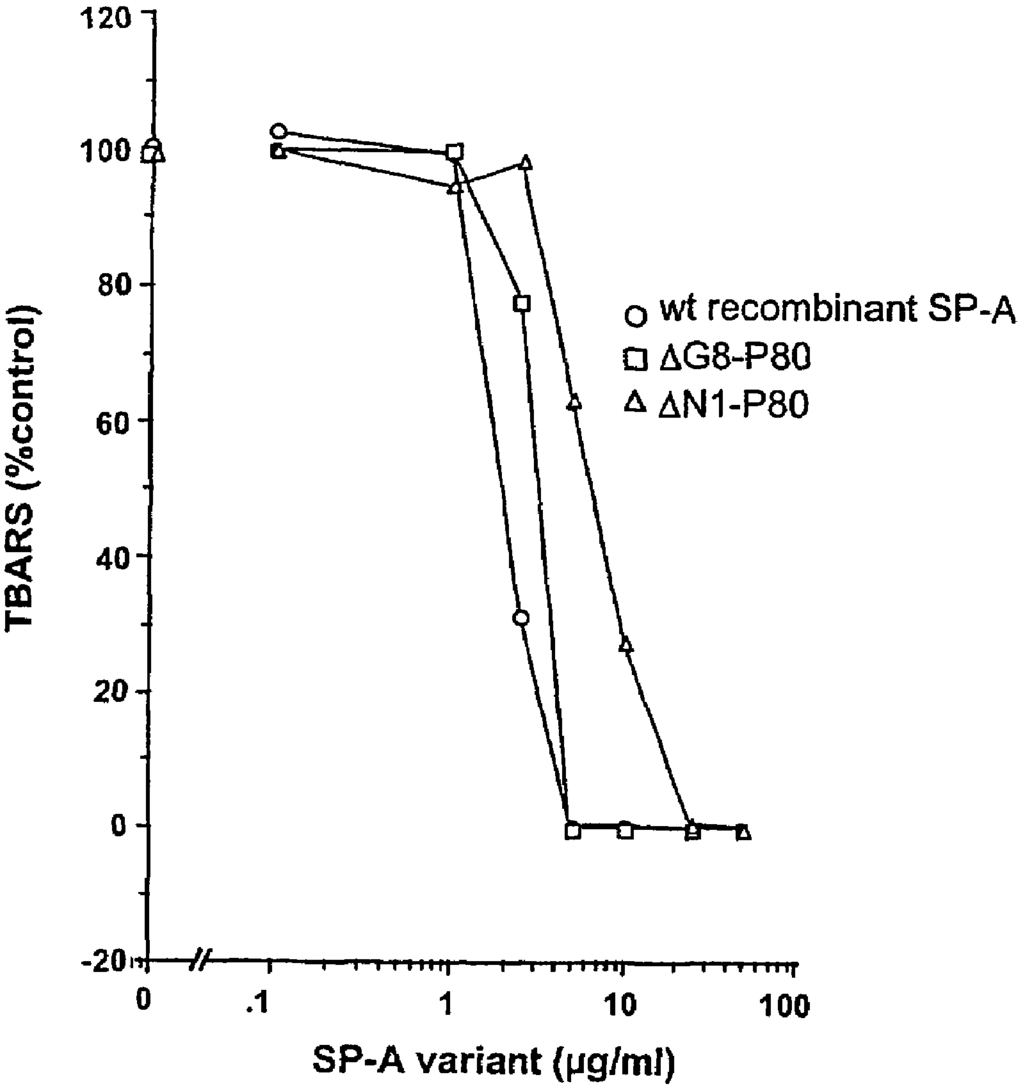
FIG. 3 depicts the structural analysis of antioxidant function of SP-A as quantified by the TBARS assay.

To determine the domain(s) of SP-A that are responsible for protection from copper-induced oxidation of LDL and synthetic lipids, the activities of mutant recombinant SP-As containing deletions in N-terminal domains were tested in the TBARS assay. The data are set forth graphically in FIG. 3. Various concentrations of recombinant wild type SP-A (circle), mutant SP-A containing a deletion of the collagen-like domain (square) and mutant SP-A containing only the neck and C-lectin domain (CLD) (triangle) were incubated with LDL in the presence of 10 μM $Cu^{2+}$, and lipid peroxidation was quantified by TBARS assay. Data are means, n=3-4.

Wild type recombinant SP-A inhibited copper-induced oxidation of LDL to the half-maximal point at 2.1 μg/ml and to basal levels at 5.0 μg/ml. A mutant SP-A containing a deletion of the collagen-like region (ΔG8-P80, McCormack et al., *J. Biol. Chem.* 272:27971-27979 (1997)), but retaining the N-terminal segment and interchain disulfide bounds, was nearly as active as the wild type recombinant protein (I.C.$_{50}$=2.8 μg/ml). A non-disulfide crosslinked trimeric construct composed solely of the neck and CLD region of the protein (ΔN1-P80, McCormack et al., *J. Biol. Chem.* 274: 3173-3183 (1999)) was also a potent antioxidant, with an I.C.$_{50}$ of 6.7 μg/ml. Although carbohydrates are known to have antioxidant properties, the protection of lipids by SP-A was not attributable to the oligosaccharide attached to Asn187, since a nonglycosylated neck and CLD construct containing an Asn187Ser mutation also inhibited lipid oxidation (ΔN1-P80,N187S), as indicated in Table 1. While not being bound by theory, it is believed that the antioxidant activity of SP-A is localized to the polypeptide sequences in the C-terminal (neck+CLD) domains of the proteins.

Figure 4:
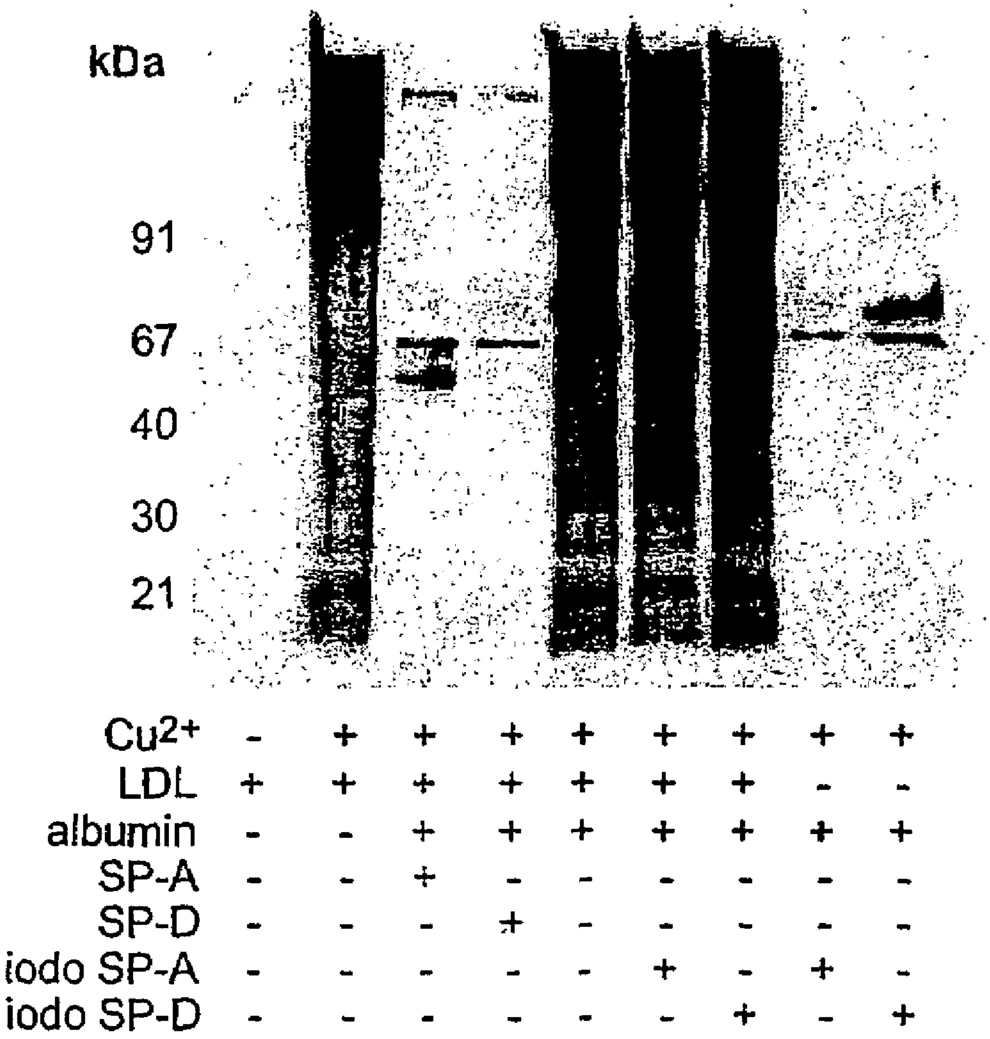
FIG. 4 depicts the immunoblot analysis of protein carbonyl derivatives formed during copper mediated LDL oxidation.

To determine if the surfactant proteins act as sinks for reactive lipid intermediates, covalent modification of SP-A and SP-D during LDL oxidation was assessed using a western analysis technique that detects carbonyl adducts (Levine et al., *Methods Enzymol.* 186: 464-78 (1990)). As depicted by FIG. 4, oxidative modification of proteins that occurred during copper induced LDL oxidation were determined by Western analysis using an antibody to DNPderivatized carbonyl moieties. Reaction mixtures contained LDL only, LDL+$Cu^{2+}$, LDL+$Cu^{2+}$+albumin+10 μg/ml SP-A, LDL+$Cu^{2+}$+albumin+1 μg/ml SP-D, LDL+$Cu^{2+}$+albumin, LDL+$Cu^{2+}$+albumin+50 μg/ml iodoacetamide treated SP-A, LDL+$Cu^{2+}$+albumin+10 μg/ml iodoacetamide treated SP-D, 50 μg/ml albumin+50 μg/ml iodoacetamide treated SP-A, albumin+10 μg/ml iodoacetamide treated SP-D.

Oxidation of LDL produced a dense high molecular weight band that corresponded to B-100, the 514 kDa protein component of LDL, and several smaller bands. Incubation with 10 μg/ml SP-A or 1 μg/ml of SP-D blocked LDL oxidation without the appearance of carbonyl-modified species at the expected molecular weights for SP-A or SP-D of 26-38 kDa or 42 kDa, respectively. However, when the surfactant proteins were inactivated by treatment with iodoacetamide, neither alkylated SP-A at 50 μg/ml or alkylated SP-D at 10 μg/ml inhibited lipid oxidation. The appearance of carbonyl derivatized SP-A species at 26, 32 and 38 kDa in the oxidized but not in the minus copper control lane is consistent with oxidative modification of the iodoacetamide-treated SP-A. Carbonyl modification of iodoacetamide treated SP-D was more difficult to assess due to lower levels of SP-D in the mixture and the complexity of bands near 40 kDa. While not being bound by theory, it is believed that SP-A and SP-D block copper-induced lipid oxidation by a mechanism that does not include carbonyl derivatization of the collectins themselves.

Effects of pulmonary collectins on oxidant-induced cell death

Figure 5:
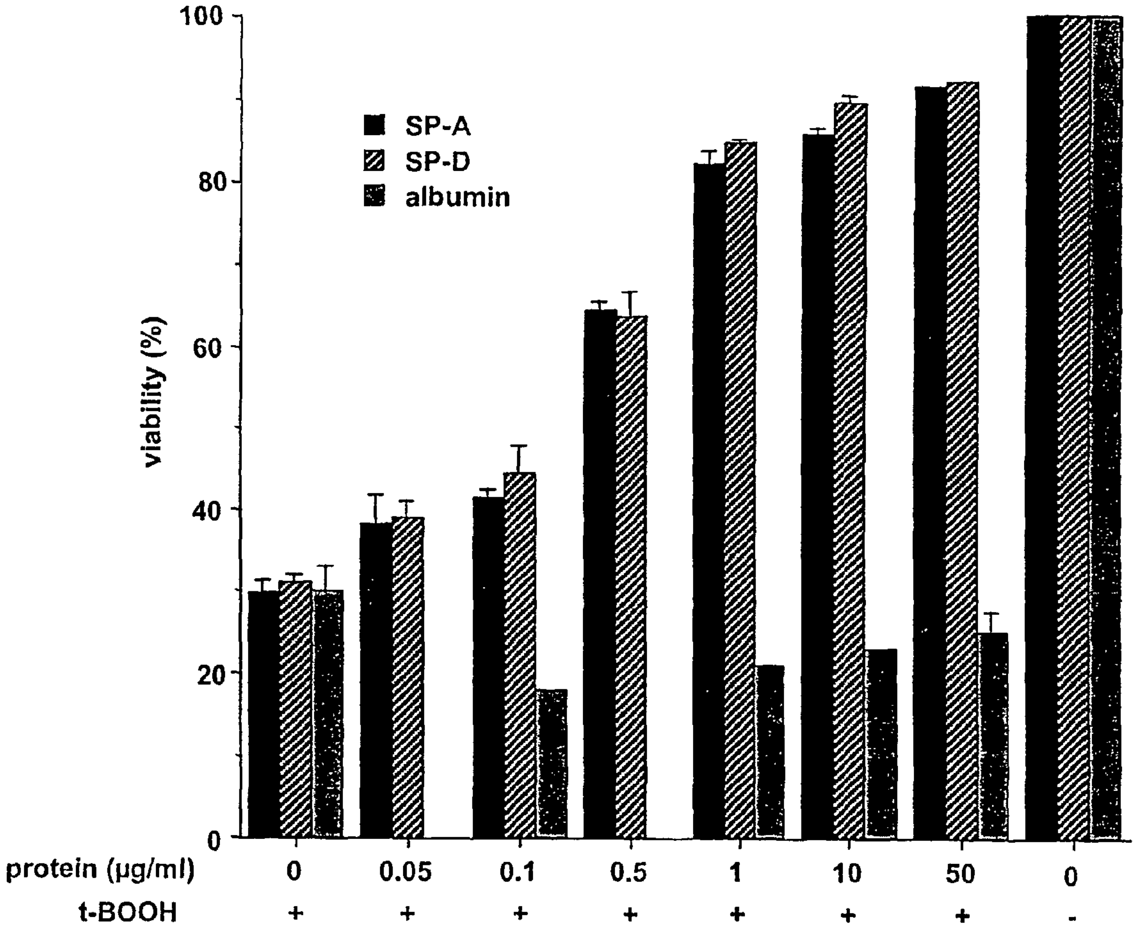
FIG. 5 depicts the protection from tert-butyl hydroperoxide (t-BOOH) induced cell death by SP-A and SP-D.

Exposure of cultured mammalian cells to tert-butylhydroperoxide (t-BOOH) promotes a variety of toxic events including depletion of glutathione, mitochondrial dysfunction and peroxidation of membrane lipids, as described in Sestili et al., *FEBS Lett.* 457(1):139-143 (1999). To determine if SP-A and SP-D protect cells from oxidative stress, RAW 264.7 murine macrophages were exposed to 40 μM t-BOOH for 24 hrs in the presence of SP-A or SP-D at concentrations from 0.01 to 50 μg/ml. Cell death was assessed by staining cells with the vital dye Trypan Blue. As depicted by FIG. 5, RAW 264.7 macrophages were incubated with various concentrations of SP-A or SP-D and 40 μM t-BOOH. Cell viability was assessed by counting the percentage of cells that excluded the vital dye Trypan Blue. Data are mean±S.E.M., n=3 for collectins except 50 μg/ml point where n=2.

It was found that both SP-A and SP-D protected RAW cells from t-BOOH-induced death in a dose-dependent fashion that was half maximal at concentrations of 0.52 μg/ml for SP-A and 0.56 μg/ml for SP-D, and which reached a plateau at a concentration of approximately 1 μg/ml for both proteins. These data indicate that SP-A and SP-D protect macrophages from oxidant stress.

The experimental results indicate that SP-A and SP-D have potent, direct antioxidant properties at concentrations that are well within their physiologic ranges. The antioxidant activity of SP-A is found in the C-terminal region of the protein, which includes the C-type lectin domain. The C-type lectin family is noted for functional diversity as pattern recognition dependent opsonins, cell adhesion molecules, cell surface receptors and anti-freeze proteins (Drickamer, K. (1999) *Curr. Opin. Struct. Biol.* 9(5):585-590 (1999)). The antioxidant function may be unique to the pulmonary collectin subgroup of the C-type lectins, however, since neither the structurally-related complement protein, C1q, or the highly homologous serum collectin, mannose binding protein A (MBP-A), had antioxidant activity.

The mechanism by which pulmonary collectins protect lipids from oxidation was examined using several approaches. Collectin mediated copper chelation does not account for the antioxidant properties, since there was a greater than $10^4$ fold molar excess of copper to collectin in reactions that demonstrated complete inhibition of oxidation. In addition, neither the occupation of the SP-A metal binding site by coincubation with 2 mM $Ca^{2+}$ or presaturation of SP-A with copper blocked the antioxidant activity of the protein. The stoichiometry of the reaction also indicates substrate sequestration is an implausible antioxidant mechanism, since at inhibitory concentrations the molar ratios of surfactant phospholipid:protein were >$10^4$ for SP-A and >$10^6$ for SP-D. That the surfactant proteins may have altered the accessibility of the lipid vesicles to copper or free radicals by causing aggregation was considered, but SP-D does not aggregate phosphatidylcholine vesicles and experiments were done under calcium-free and physiologic pH conditions which do not support aggregation by SP-A (Efrati et al., *Biochemistry* 26:7986-7993 (1987) and Hawgood et al., Biochemistry 24:184-190 (1985)). The proteins do not themselves become modified during lipid oxidation and therefore do not protect lipids by functioning as 'suicide' sinks for covalent attack by reactive lipid intermediates. SP-A and SP-D arrest LDL oxidation almost instantaneously despite the inaccessibility of the hydrophilic surfactant proteins to oxidizable substrates in the interior of the particle. Collectively, the data indicate that the collectins directly interfere with lipid oxidation by inhibiting the formation of lipid radicals or acting as free radical chain terminators. The CLD of SP-A and SP-D are rich in aromatic amino acids which are candidates for the quenching of free radicals.

The pulmonary collectins also protect growing cells from oxidant stress. The mechanism of t-BOOH-induced cell death is thought to be dependent on metal ions (Miyata et al., *Nat. Genet.* 14(1), 55-61(1996)), mediated by free radicals generated through the iron-dependent Fenton reaction (Buettner et al., *Arch. Biochem. Biophys.* 300(2), 535-543 (1993)) or by copper-induced oxidation of lipid hydroperoxides (Patel et al., *Biochem. J.* 322(Pt 2):425-433(1997)). SP-A and SP-D are large hydrophilic molecules that almost certainly exert their antioxidant effects in the extracellular compartment. Based on the results of the lipid oxidation experiments, it is believed that the lung collectins protect cells by interfering with the formation of free radicals or free radical chain termination. It is possible, however, that the proteins alter the cellular response to oxidant stress by binding to cell surface molecules and activating signaling pathways.

The lung is exposed to oxidant stress through inhalation of oxygen present in the atmosphere, the presence of ozone and trace metals in air pollutants, and oxidant species released from macrophages and neutrophils in the ELF. In addition, the ELF from normal subjects has been shown to contain chelatable redox active iron that is derived from endogenous sources (Gutteridge et al., *Biochem. Biophys. Res. Commun.* 220(3), 1024-1027 (1996)). Although surfactant is inherently resistant to oxidation due to the preponderance of saturated phospholipids, oxidizable cholesterol and unsaturated phospholipids represent 40% of the weight of surfactant, and 15% of all surfactant phospholipids contain two or more double bonds (Postle et al., *Am. J. Respir. Cell. Mol. Biol.* 20(1), 90-98 (1999)). The properties of SP-A and SP-D to inhibit the propagation of free radical chain reactions may prevent waves of lipid oxidation from spreading through the 100 $m^2$ surfactant interface. Since SP-A is intimately associated with surfactant lipids and aggregates in the airspace, and SP-D is found primarily free in the ELF, while not being bound by theory, it is believed that the pulmonary collectins perform complementary functions to protect the lipid interfaces and the aqueous compartment of the ELF from oxidative stress. Recent data from collectin-deficient animal models is considered to be consistent with this notion. The SP-D deficient gene-targeted mouse, which also had reduced SP-A levels, had enhanced oxidant production in the lung and developed a surfactant lipid clearance defect (Wert et al., *Proc. Natl. Acad. Sci. USA* 97(11): 5972-5977 (2000); Botas et al., *S. Proc. Natl. Acad. Sci. USA* 95(20):11869-11874 (1998); and Korfhagen et al., J Biol Chem 273(43):28438-28443 (1998)). The lack of SP-D increased hydrogen peroxide production by isolated alveolar macrophages, but an direct, acellular antioxidant role for SP-D was not examined in those studies (Wert et al., *Proc. Natl. Acad. Sci. USA* 97(11):5972-5977 (2000)). On the other hand, the SP-A deficient gene-targeted mouse, which had normal SP-D levels, did not have a clear surfactant homeostasis phenotype (Korfhagen et al., *Proc. Natl. Acad. Sci.* 93, 9594-9599 (1996)). While not being bound by theory, it is believed that combined SP-A and SP-D deficiency in the SP-D null mouse results in surfactant oxidation that overwhelms the clearance capacity of surfactant metabolizing enzymes, but that sufficient SP-D is present in the SP-A null mouse to protect the surfactant system from oxidative injury.

The recent observation that all of the major vertebrate groups have lung collectins in their airspaces, including the most primitive amphibious fish, underscores the fundamental importance of these proteins to pulmonary function (Gutteridge et al., *Biochem. Biophys. Res. Commun.* 220(3), 1024-1027 (1996) and Sullivan et al., *J. Mol. Evol.* 46, 131-138 (1998)). The harmful effects of air breathing on the oxidation sensitive cellular and molecular components at the environmental interface of the lung may be mitigated by the presence of surfactant proteins A and D.

Purification and modification of surfactant proteins-antimicrobial properties

Native SP-A and SP-D were isolated from the alveolar wash of rats which had been pretreated with intratracheal silica to enhance the collectin yield, in accordance with the method of Dethloff et al., *Biochem. J.* 233:111-118 (1986). After centrifugation, rat SP-D was purified by maltose-Sepharose affinity chromatography of the supernatant and rat SP-A was purified from the pellet by NaBr flotation, butanol extraction and mannose-Sepharose affinity chromatography, in accordance with the method of McCormack et al., *J. Biol. Chem.* 272:27971-27979 (1997). Mouse SP-D was used interchangeably with rat SP-D. All proteins were extensively dialyzed to remove residual EDTA. For some experiments, rat SP-A and rat SP-D were alkylated by incubation with 0.5 M iodoacetamide at 37° C. in the dark for 1 hr and then extensively dialyzed. The wild type and mutant recombinant SP-A, SP-D and MBP used in this study were synthesized using baculovirus vectors and purified by carbohydrate-Sepharose affinity chromatography, as previously described in McCormack et al., *J. Biol Chem.* 272: 27971-27979 (1997); McCormack et al., *Biochemistry* 36:13963-13971 (1997); and McCormack et al., *J. Biol. Chem.* 274:3173-3183 (1999).

SP-A and SP-D attenuate light scattering by growing *E. coli* in a LPS-reversible manner Experiments were designed to assess the effect of SP-A on the growth and viability of bacterial organisms. For these experiments, SP-A isolated from patients with alveolar proteinosis (APP-SP-A) was used, because it is available in greater abundance than the rat reagents. *E. coli* (FIGS. 7A,B,D) or GBS (FIG. 7C) organisms that had been grown to stationary phase overnight were diluted in Luria broth or Todd-Hewitt broth, respectively and agitated at 37° C. for five hours in the presence or absence of APP-SP-A(FIGS. 7A,B,C) or SP-D (FIG. 7D). Bacterial growth was monitored by measuring light scattering in a spectrophotometer at a wavelength of 400 nm. In the absence of collecting, both GBS (FIG. 7C) and *E. coli* (FIGS. 7A,B,D) grew logarithmically and light scattering increased steadily over the six hour incubation approaching a peak 6 hr. optical density ($O.D._{400\ nm}$) of approximately 2.0-3.0 units. APP-SP-A had no effect on the increase in light scattering due to growing GBS (FIG. 7C). For *E. coli*, however, the increase in light scattering was partially inhibited by 25 μg/ml APP-SP-A (peak $O.D._{400\ nm}$ of 1.25 units), and almost completely inhibited by 250 μg/ml APP-SP-A (maximal $O.D._{400\ nm}$ of 0.25 units) (FIG. 7A).

Figure 7:
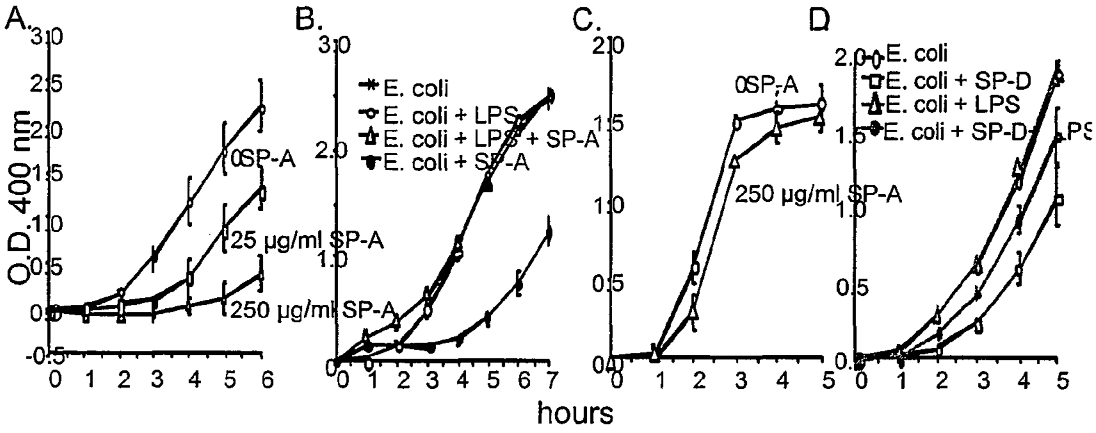
FIG. 7 depicts the attenuation of light scattering by growing *E. coli* in the presence of SP-A or SP-D.

To determine if growth inhibition by SP-A was dependent on the interaction of the protein with LPS on the bacterial surface, *E. coli* growth inhibition was accessed by APP-SP-A in the presence and absence of excess J5 LPS vesicles. As shown in FIG. 7 B and D, the time dependent increase in light scattering was inhibited by 100 μg/ml APP-SP-A or SP-D and was not affected by J5 LPS vesicles alone. However, SP-A and SP-D mediated attenuation of light scattering produced by growing *E. coli* was completely and partially blocked by 300 μg/ml J5 LPS vesicles, respectively. These data indicate that SP-A and SP-D associate with gram negative bacteria in an LPS dependent manner to reduce light scattering from microbial proliferation.

SP-A and SP-D directly inhibit bacterial growth

Figure 8:
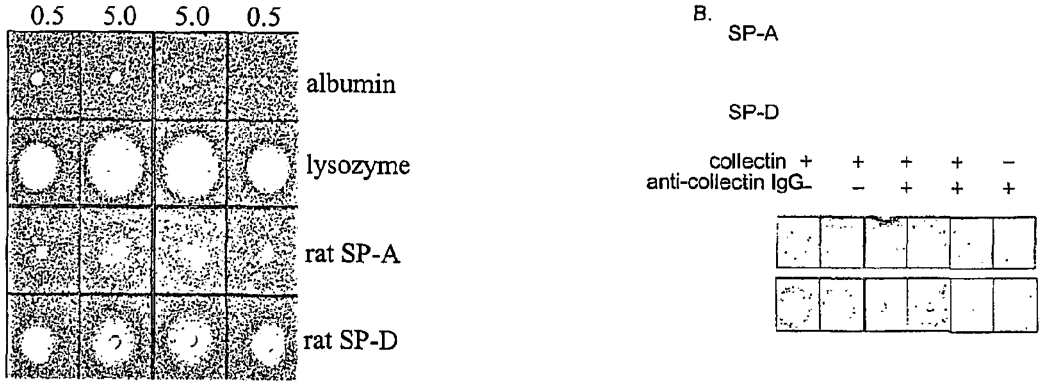
FIG. 8 depicts the inhibition of *E. coli* growth in the presence of SP-A or SP-D.
Figure 9:
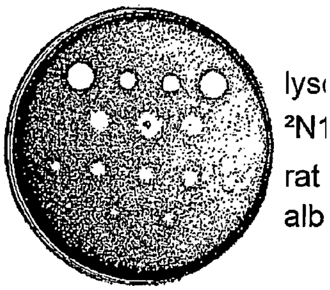
FIG. 9 depicts the inhibition of *E. coli* growth in the presence of SP-A regarding the N-terminal domain.

The attenuation of light scattering by SP-A and SP-D could be due to bacterial aggregation, inhibition of growth or a combination of both. For SP-A, the number of CFUs at each time point over a six hour incubation decreased by 90% at 1 and 2 hrs, and then resumed a logarithmic growth rate over the next 3-5 hours. Light microscopic examination of the bacterial cultures after 1 hour incubation with APP-SP-A revealed extensive bacterial aggregation, which confounds the assessment of bacterial viability. A radial diffusion method was therefore used to examine the effect of the collectins and their individual structural domains on the growth of *E. coli* that were immobilized in agar (FIGS. 8,9). Wells were bored into plates containing agar impregnated with $2\times10^6$ *E. coli*/ml or GBS. Proteins to be tested were introduced into the wells and the plates were incubated overnight at 37° C. Positive control protein lysozyme at 0.5 and 5.0 μg added produced dose-dependent clearing in both the *E. coli* plates and the GBS plates, but negative control protein albumin at 5 μg had no effect. Rat SP-A and SP-D inhibited the growth of *E. coli* K12 (FIG. 8,9) but not GBS (not shown). The ΔN1-P80 (see mutant in FIG. 6C) SP-A also produced detectable clearing in the *E. coli* plates at 0.5 μg and easily visible inhibition of bacterial growth at 5 μg (FIG. 9). These data indicate that SP-A inhibits the growth of *E. coli* (but not GBS) by a C-terminal domain dependent mechanism. Inhibition of *E. coli* growth by recombinant mouse SP-A and SP-D were blocked with anti-mouse SP-A and anti-mouse SP-D antibodies, respectively (FIG. 8B) and by excess LPS vesicles (for SP-A>SP-D) (FIG. 8C). These results suggest that growth inhibition by our SP-A and SP-D preparations are LPS dependent, and that the collectins themselves rather than copurifying antimicrobials (such as EDTA or azide that may inadvertently leach from the columns) are responsible for the growth inhibitory effect. SP-A also inhibited the growth of *P. aeruginosa* (PAO1 mutant) in a radial diffusion assay.

Outer membrane protein A protects *E. coli* from growth inhibition by SP-A and SP-D SP-A has been reported to bind to the outer membrane protein (OmpA) of Hemophilus influenza, a porin that facilitates the uptake of nutrients from the environment. The hypothesis that binding of collectins to OmpA mediates bacterial growth inhibition by SP-A and SP-D was tested. These experiments were performed using a genetically engineered clinical isolate of *E. coli* that was rendered OmpA deficient (ΔOmpA) by transposon mutagenesis. SP-A and SP-D inhibited the growth of the parental *E. coli* strain (E69), but growth inhibition was increased (judged by the radius of clearing around the well) by the genetic deletion of OmpA (FIG. 10). Replacement of OmpA in the ΔOmpA bacteria by plasmid driven OmpA expression attenuated growth inhibition by SP-A and SP-D, but the ΔOmpA organism that contained an empty vector control was inhibited to the same extent as the ΔOmpA organism. These data indicate that OmpA protects *E. coli* from growth inhibition by SP-A and SP-D and suggests that SP-A and SP-D may exert their effects at the level of the cell membrane.

SP-A inhibits protein synthesis in *Histoplasma capsulatum*

Figure 11:
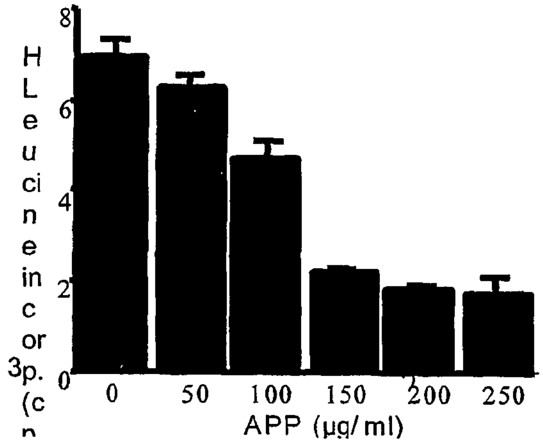
FIG. 11 depicts SP-A inhibition of protein synthesis in *H. capsulatum;*

As depicted by FIG. 11, SP-A directly inhibits the incorporation of $^3$H-leucine into *H. capsulatum* in a dose-dependent manner that reaches a maximal effect at about 150 μg/ml APP-SP-A. These data indicate that the inhibition of microbial growth by the collectins is not specific to bacteria.

SP-A can inhibit and reverse light scattering due to aggregation of vesicles composed of *E. coli* Phospholipids As depicted by FIG. 12, *E coli* phospholipid vesicles generated by probe sonication were aggregated by addition of $Ca^{2+}$(□). SP-A decreased aggregation when added at 0 time (Δ), and SP-A added at 8 minutes reversed established aggregation (μ) in a manner that was similar to addition of 10 mM EDTA at 8 minutes (□). SP-A also inhibited the aggregation of *E. coli* J5 LPS, but did not reverse established aggregation by J5 LPS vesicles (not shown). In contrast, SP-A mediates aggregation of surfactant liposomes. This system will be useful for modeling the structural basis of the interaction between collectins and bacterial membranes.

SP-A and SP-D form complexes with metals.

SP-A and SP-D block lipid peroxidation (LPO) that is produced by 24 hr incubation by 10 μM copper or iron. Recent preliminary data presented above indicates that the antioxidant properties of SP-A and SP-D require complex formation with transition metals (FIG. 13). In these experiments, LPO of model surfactant lipids was initiated with the free radical generating compound 2,2'-azobisisobutyronitrile (AIBN). SP-A and SP-D did not inhibit LPO, unless copper was added at low concentrations. Copper did not contribute to LPO under the experimental conditions employed, due to the short incubation period (3 hours). Zinc could not substitute for copper in these experiments, but iron could (not shown). These data indicate that SP-A and SP-D form complexes with transition metals. The association of the collectins with metals may not only confer antioxidant properties on the proteins but may also destabilize bacterial membranes or limit bacterial growth by producing an iron (or other metal) deficient environment.

Through-out the specification, parts and percentages are by weight unless otherwise indicated. Additional embodiments and modifications within the scope of the claimed invention will be apparent to one of ordinary skill in the art. Accordingly, the scope of the present invention shall be considered in the terms of the following claims, and is understood not to be limited to the details, examples or the methods described in the specification.

What is claimed is:

1. A method of treating a patient for acute lung injury comprising administering to the patient an effective antimicrobial amount of an antimicrobial lung surfactant protein compound, wherein the antimicrobial lung surfactant protein compound is a peptide comprising the amino acid sequence: Met-Phe-Leu-Lys-Ala-Val-Val-Leu-Thr-Val-Ala-Leu-Val-Ala-Ile-Thr-Gly-Thr-Gln-Ala-Glu-Val-Thr-Ser-Asp-Gln-Val-Ala-Asn-Val (SEQ ID NO:1).

2. A method of treating patient for acute lung injury comprising administering to the patient an effective antioxidation amount of an antioxidant lung surfactant protein compound comprising the amino acid sequence: Met-Phe-Leu-Lys-Ala-Val-Val-Leu-Thr-Val-Ala-Leu-Val-Ala-Ile-Thr-Gly-Thr-Gln-Ala-Glu-Val-Thr-Ser-Asp-Gln-Val-Ala-Asn-Val (SEQ ID NO:1).

* * * * *

SEQUENCE LISTING

```
<160> NUMBER OF SEQ ID NOS: 17

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Antioxidant
      Peptide

<400> SEQUENCE: 1

Met Phe Leu Lys Ala Val Val Leu Thr Val Ala Leu Val Ala Ile Thr
1               5                   10                  15

Gly Thr Gln Ala Glu Val Thr Ser Asp Gln Val Ala Asn Val
            20                  25                  30


<210> SEQ ID NO 2
<211> LENGTH: 148
<212> TYPE: PRT
<213> ORGANISM: Rat

<400> SEQUENCE: 2
```

-continued

```
Ala Tyr Leu Asp Glu Glu Leu Gln Thr Glu Leu Tyr Glu Ile Lys His
1               5                   10                  15

Gln Ile Leu Gln Thr Met Gly Val Leu Ser Leu Gln Gly Ser Met Leu
            20                  25                  30

Ser Val Gly Asp Lys Val Ser Thr Asn Gly Gln Ser Val Asn Phe Asp
        35                  40                  45

Thr Ile Lys Glu Met Cys Thr Phe Arg Ala Gly Gly Asn Ile Ala Val
    50                  55                  60

Pro Arg Thr Pro Glu Glu Asn Glu Ala Ile Ala Ser Ile Ala Lys Lys
65                  70                  75                  80

Tyr Asn Asn Tyr Val Tyr Leu Gly Met Ile Glu Asp Gln Thr Pro Gly
                85                  90                  95

Asp Phe His Tyr Leu Asp Gly Ala Ser Val Asn Tyr Thr Asn Trp Tyr
            100                 105                 110

Pro Gly Glu Pro Arg Gly Gln Gly Lys Glu Lys Cys Val Glu Met Tyr
        115                 120                 125

Thr Asp Gly Thr Trp Asn Asp Arg Gly Cys Leu Gln Tyr Arg Leu Ala
    130                 135                 140

Val Cys Glu Phe
145


<210> SEQ ID NO 3
<211> LENGTH: 93
<212> TYPE: PRT
<213> ORGANISM: Rat

<400> SEQUENCE: 3

Ala Tyr Leu Asp Glu Glu Leu Gln Thr Glu Leu Tyr Glu Ile Lys His
1               5                   10                  15

Gln Ile Leu Gln Thr Met Gly Val Leu Ser Leu Gln Gly Ser Met Leu
            20                  25                  30

Ser Val Gly Asp Lys Val Ser Thr Asn Gly Gln Ser Val Asn Phe Asp
        35                  40                  45

Thr Ile Lys Glu Met Cys Thr Phe Arg Ala Gly Gly Asn Ile Ala Val
    50                  55                  60

Pro Arg Thr Pro Glu Glu Asn Glu Ala Ile Ala Ser Ile Ala Lys Lys
65                  70                  75                  80

Tyr Asn Asn Tyr Val Tyr Leu Gly Met Ile Glu Asp Gln
                85                  90


<210> SEQ ID NO 4
<211> LENGTH: 248
<212> TYPE: PRT
<213> ORGANISM: Homo sapiens

<400> SEQUENCE: 4

Met Trp Leu Cys Pro Leu Ala Leu Thr Leu Ile Leu Met Ala Ala Ser
1               5                   10                  15

Gly Ala Ala Cys Glu Val Lys Asp Val Cys Val Gly Ser Pro Gly Ile
            20                  25                  30

Pro Gly Thr Pro Gly Ser His Gly Leu Pro Gly Arg Asp Gly Arg Asp
        35                  40                  45

Gly Val Lys Gly Asp Pro Gly Pro Pro Gly Pro Met Gly Pro Pro Gly
    50                  55                  60

Glu Thr Pro Cys Pro Pro Gly Asn Asn Gly Leu Pro Gly Ala Pro Gly
65                  70                  75                  80
```

-continued

```
Val Pro Gly Glu Arg Gly Glu Lys Gly Glu Pro Gly Glu Arg Gly Pro
                85                  90                  95

Pro Gly Leu Pro Ala His Leu Asp Glu Glu Leu Gln Ala Thr Leu His
            100                 105                 110

Asp Phe Arg His Gln Ile Leu Gln Thr Arg Gly Ala Leu Ser Leu Gln
        115                 120                 125

Gly Ser Ile Met Thr Val Gly Glu Lys Val Phe Ser Ser Asn Gly Gln
    130                 135                 140

Ser Ile Thr Phe Asp Ala Ile Gln Glu Ala Cys Ala Arg Ala Gly Gly
145                 150                 155                 160

Arg Ile Ala Val Pro Arg Asn Pro Glu Glu Asn Glu Ala Ile Ala Ser
                165                 170                 175

Phe Val Lys Lys Tyr Asn Thr Tyr Ala Tyr Val Gly Leu Thr Glu Gly
            180                 185                 190

Pro Ser Pro Gly Asp Phe Arg Tyr Ser Asp Gly Thr Pro Val Asn Tyr
        195                 200                 205

Thr Asn Trp Tyr Arg Gly Glu Pro Ala Gly Arg Gly Lys Glu Gln Cys
    210                 215                 220

Val Glu Met Tyr Thr Asp Gly Gln Trp Asn Asp Arg Asn Cys Leu Tyr
225                 230                 235                 240

Ser Arg Leu Thr Ile Cys Glu Phe
                245


<210> SEQ ID NO 5
<211> LENGTH: 148
<212> TYPE: PRT
<213> ORGANISM: Homo sapiens

<400> SEQUENCE: 5

Ala His Leu Asp Glu Glu Leu Gln Ala Thr Leu His Asp Phe Arg His
1               5                   10                  15

Gln Ile Leu Gln Thr Arg Gly Ala Leu Ser Leu Gln Gly Ser Ile Met
            20                  25                  30

Thr Val Gly Glu Lys Val Phe Ser Ser Asn Gly Gln Ser Ile Thr Phe
        35                  40                  45

Asp Ala Ile Gln Glu Ala Cys Ala Arg Ala Gly Gly Arg Ile Ala Val
    50                  55                  60

Pro Arg Asn Pro Glu Glu Asn Glu Ala Ile Ala Ser Phe Val Lys Lys
65                  70                  75                  80

Tyr Asn Thr Tyr Ala Tyr Val Gly Leu Thr Glu Gly Pro Ser Pro Gly
                85                  90                  95

Asp Phe Arg Tyr Ser Asp Gly Thr Pro Val Asn Tyr Thr Asn Trp Tyr
            100                 105                 110

Arg Gly Glu Pro Ala Gly Arg Gly Lys Glu Gln Cys Val Glu Met Tyr
        115                 120                 125

Thr Asp Gly Gln Trp Asn Asp Arg Asn Cys Leu Tyr Ser Arg Leu Thr
    130                 135                 140

Ile Cys Glu Phe
145


<210> SEQ ID NO 6
<211> LENGTH: 93
<212> TYPE: PRT
<213> ORGANISM: Homo sapiens

<400> SEQUENCE: 6
```

-continued

```
Ala His Leu Asp Glu Glu Leu Gln Ala Thr Leu His Asp Phe Arg His
1               5                   10                  15

Gln Ile Leu Gln Thr Arg Gly Ala Leu Ser Leu Gln Gly Ser Ile Met
            20                  25                  30

Thr Val Gly Glu Lys Val Phe Ser Ser Asn Gly Gln Ser Ile Thr Phe
        35                  40                  45

Asp Ala Ile Gln Glu Ala Cys Ala Arg Ala Gly Gly Arg Ile Ala Val
    50                  55                  60

Pro Arg Asn Pro Glu Glu Asn Glu Ala Ile Ala Ser Phe Val Lys Lys
65                  70                  75                  80

Tyr Asn Thr Tyr Ala Tyr Val Gly Leu Thr Glu Gly Pro
                85                  90


<210> SEQ ID NO 7
<211> LENGTH: 374
<212> TYPE: PRT
<213> ORGANISM: Rat

<400> SEQUENCE: 7

Met Leu His Phe Leu Ser Met Leu Val Leu Leu Val Gln Pro Leu Gly
1               5                   10                  15

Asp Leu Gly Ala Glu Met Lys Thr Leu Ser Gln Arg Ser Ile Thr Asn
            20                  25                  30

Thr Cys Thr Leu Val Leu Cys Ser Pro Thr Glu Asn Gly Leu Pro Gly
        35                  40                  45

Arg Asp Gly Arg Asp Gly Arg Glu Gly Pro Arg Gly Glu Lys Gly Asp
    50                  55                  60

Pro Gly Leu Pro Gly Pro Met Gly Leu Ser Gly Leu Pro Gly Pro Arg
65                  70                  75                  80

Gly Pro Val Gly Pro Lys Gly Glu Asn Gly Ser Ala Gly Glu Pro Gly
                85                  90                  95

Pro Lys Gly Glu Arg Gly Leu Val Gly Pro Pro Gly Ser Pro Gly Ile
            100                 105                 110

Ser Gly Pro Ala Gly Lys Glu Gly Pro Ser Gly Lys Gln Gly Asn Ile
        115                 120                 125

Gly Pro Gln Gly Lys Pro Gly Pro Lys Gly Glu Ala Gly Pro Lys Gly
    130                 135                 140

Glu Val Gly Ala Pro Gly Met Gln Gly Ser Ala Gly Ala Lys Gly Pro
145                 150                 155                 160

Ala Gly Pro Lys Gly Glu Arg Gly Ala Pro Gly Glu Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Ala
        195                 200                 205

Pro Gly Asp Arg Gly Ile Lys Gly Glu Ser Gly Leu Pro Asp Ser Ala
    210                 215                 220

Ala Leu Arg Gln Gln Met Glu Ala Leu Asn Gly Lys Leu Gln Arg Leu
225                 230                 235                 240

Glu Ala Ala Phe Ser Arg Tyr Lys Lys Ala Ala Leu Phe Pro Asp Gly
                245                 250                 255

Gln Ser Val Gly Asp Lys Ile Phe Arg Ala Ala Asn Ser Glu Glu Pro
            260                 265                 270

Phe Glu Asp Ala Lys Glu Met Cys Arg Gln Ala Gly Gly Gln Leu Ala
```

-continued

```
        275                 280                 285

Ser Pro Arg Ser Ala Thr Glu Asn Ala Ala Val Gln Gln Leu Val Thr
    290                 295                 300

Ala His Ser Lys Ala Ala Phe Leu Ser Met Thr Asp Val Gly Thr Glu
305                 310                 315                 320

Gly Lys Phe Thr Tyr Pro Thr Gly Glu Ala Leu Val Tyr Ser Asn Trp
                325                 330                 335

Ala Pro Gly Glu Pro Asn Asn Asn Gly Gly Ala Glu Asn Cys Val Glu
            340                 345                 350

Ile Phe Thr Asn Gly Gln Trp Asn Asp Lys Ala Cys Gly Glu Gln Arg
        355                 360                 365

Leu Val Ile Cys Glu Phe
    370


<210> SEQ ID NO 8
<211> LENGTH: 153
<212> TYPE: PRT
<213> ORGANISM: Rat

<400> SEQUENCE: 8

Asp Ser Ala Ala Leu Arg Gln Gln Met Glu Ala Leu Asn Gly Lys Leu
1               5                   10                  15

Gln Arg Leu Glu Ala Ala Phe Ser Arg Tyr Lys Lys Ala Ala Leu Phe
            20                  25                  30

Pro Asp Gly Gln Ser Val Gly Asp Lys Ile Phe Arg Ala Ala Asn Ser
        35                  40                  45

Glu Glu Pro Phe Glu Asp Ala Lys Glu Met Cys Arg Gln Ala Gly Gly
    50                  55                  60

Gln Leu Ala Ser Pro Arg Ser Ala Thr Glu Asn Ala Ala Val Gln Gln
65                  70                  75                  80

Leu Val Thr Ala His Ser Lys Ala Ala Phe Leu Ser Met Thr Asp Val
                85                  90                  95

Gly Thr Glu Gly Lys Phe Thr Tyr Pro Thr Gly Glu Ala Leu Val Tyr
            100                 105                 110

Ser Asn Trp Ala Pro Gly Glu Pro Asn Asn Asn Gly Gly Ala Glu Asn
        115                 120                 125

Cys Val Glu Ile Phe Thr Asn Gly Gln Trp Asn Asp Lys Ala Cys Gly
    130                 135                 140

Glu Gln Arg Leu Val Ile Cys Glu Phe
145                 150


<210> SEQ ID NO 9
<211> LENGTH: 375
<212> TYPE: PRT
<213> ORGANISM: Homo sapiens

<400> SEQUENCE: 9

Met Leu Leu Phe Leu Leu Ser Ala Leu Val Leu Leu Thr Gln Pro Leu
1               5                   10                  15

Gly Tyr Leu Glu Ala Glu Met Lys Thr Tyr Ser His Arg Thr Met Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
```

-continued

```
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Gly Pro Pro Gly Pro Pro Gly
            100                 105                 110

Val Pro Gly Pro Ala Gly Arg Glu Gly Ala Leu Gly Lys Gln Gly Asn
        115                 120                 125

Ile Gly Pro Gln Gly Lys Pro Gly Pro Lys Gly Glu Ala Gly Pro Lys
    130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                165                 170                 175

Pro Gly Asn Thr Gly Ala Ala Gly Ser Ala Gly Ala Met Gly Pro Gln
            180                 185                 190

Gly Ser Pro Gly Ala Arg Gly Pro Pro Gly Leu Lys Gly Asp Lys Gly
        195                 200                 205

Ile Pro Gly Asp Lys Gly Ala Lys Gly Glu Ser Gly Leu Pro Asp Val
    210                 215                 220

Ala Ser Leu Arg Gln Gln Val Glu Ala Leu Gln Gly Gln Val Gln His
225                 230                 235                 240

Leu Gln Ala Ala Phe Ser Gln Tyr Lys Lys Val Glu Leu Phe Pro Asn
                245                 250                 255

Gly Gln Ser Val Gly Glu Lys Ile Phe Lys Thr Ala Gly Phe Val Lys
            260                 265                 270

Pro Phe Thr Glu Ala Gln Leu Leu Cys Thr Gln Ala Gly Gly Gln Leu
        275                 280                 285

Ala Ser Pro Arg Ser Ala Ala Glu Asn Ala Ala Leu Gln Gln Leu Val
    290                 295                 300

Val Ala Lys Asn Glu Ala Ala Phe Leu Ser Met Thr Asp Ser Lys Thr
305                 310                 315                 320

Glu Gly Lys Phe Thr Tyr Pro Thr Gly Glu Ser Leu Val Tyr Ser Asn
                325                 330                 335

Trp Ala Pro Gly Glu Pro Asn Asp Asp Gly Gly Ser Glu Asp Cys Val
            340                 345                 350

Glu Ile Phe Thr Asn Gly Lys Trp Asn Asp Arg Ala Cys Gly Glu Lys
        355                 360                 365

Arg Leu Val Val Cys Glu Phe
    370                 375


<210> SEQ ID NO 10
<211> LENGTH: 153
<212> TYPE: PRT
<213> ORGANISM: Homo sapiens

<400> SEQUENCE: 10

Asp Val Ala Ser Leu Arg Gln Gln Val Glu Ala Leu Gln Gly Gln Val
1               5                   10                  15

Gln His Leu Gln Ala Ala Phe Ser Gln Tyr Lys Lys Val Glu Leu Phe
            20                  25                  30

Pro Asn Gly Gln Ser Val Gly Glu Lys Ile Phe Lys Thr Ala Gly Phe
        35                  40                  45

Val Lys Pro Phe Thr Glu Ala Gln Leu Leu Cys Thr Gln Ala Gly Gly
    50                  55                  60
```

-continued

```
Gln Leu Ala Ser Pro Arg Ser Ala Ala Glu Asn Ala Ala Leu Gln Gln
65                  70                  75                  80

Leu Val Val Ala Lys Asn Glu Ala Ala Phe Leu Ser Met Thr Asp Ser
                85                  90                  95

Lys Thr Glu Gly Lys Phe Thr Tyr Pro Thr Gly Glu Ser Leu Val Tyr
            100                 105                 110

Ser Asn Trp Ala Pro Gly Glu Pro Asn Asp Asp Gly Gly Ser Glu Asp
        115                 120                 125

Cys Val Glu Ile Phe Thr Asn Gly Lys Trp Asn Asp Arg Ala Cys Gly
    130                 135                 140

Glu Lys Arg Leu Val Val Cys Glu Phe
145                 150


<210> SEQ ID NO 11
<211> LENGTH: 96
<212> TYPE: PRT
<213> ORGANISM: Homo sapiens

<400> SEQUENCE: 11

Asp Val Ala Ser Leu Arg Gln Gln Val Glu Ala Leu Gln Gly Gln Val
1               5                   10                  15

Gln His Leu Gln Ala Ala Phe Ser Gln Tyr Lys Lys Val Glu Leu Phe
            20                  25                  30

Pro Asn Gly Gln Ser Val Gly Glu Lys Ile Phe Lys Thr Ala Gly Phe
        35                  40                  45

Val Lys Pro Phe Thr Glu Ala Gln Leu Leu Cys Thr Gln Ala Gly Gly
    50                  55                  60

Gln Leu Ala Ser Pro Arg Ser Ala Ala Glu Asn Ala Ala Leu Gln Gln
65                  70                  75                  80

Leu Val Val Ala Lys Asn Glu Ala Ala Phe Leu Ser Met Thr Asp Ser
                85                  90                  95


<210> SEQ ID NO 12
<211> LENGTH: 248
<212> TYPE: PRT
<213> ORGANISM: Artificial Sequence
<220> FEATURE:
<223> OTHER INFORMATION: Description of Artificial Sequence: antioxidant
      peptide

<400> SEQUENCE: 12

Met Ser Leu Cys Ser Leu Ala Phe Thr Leu Phe Leu Thr Val Val Ala
1               5                   10                  15

Gly Ile Lys Cys Asn Val Thr Asp Val Cys Ala Gly Ser Pro Gly Ile
            20                  25                  30

Pro Gly Ala Pro Gly Asn His Gly Leu Pro Gly Arg Asp Gly Arg Asp
        35                  40                  45

Gly Val Lys Gly Asp Pro Gly Pro Pro Gly Pro Met Gly Pro Pro Gly
    50                  55                  60

Gly Met Pro Gly Leu Pro Gly Arg Asp Gly Leu Pro Gly Ala Pro Gly
65                  70                  75                  80

Ala Pro Gly Glu Arg Gly Asp Lys Gly Glu Pro Gly Glu Arg Gly Leu
                85                  90                  95

Pro Gly Phe Pro Ala Tyr Leu Asp Glu Glu Leu Gln Thr Glu Leu Tyr
            100                 105                 110

Glu Ile Lys His Gln Ile Leu Gln Thr Met Gly Val Leu Ser Leu Gln
        115                 120                 125
```

-continued

```
Gly Ser Met Leu Ser Val Gly Asp Lys Val Phe Ser Thr Asn Gly Gln
    130                 135                 140

Ser Val Asn Phe Asp Thr Ile Lys Glu Met Cys Thr Arg Ala Gly Gly
145                 150                 155                 160

Asn Ile Ala Val Pro Arg Thr Pro Glu Glu Asn Glu Ala Ile Ala Ser
                165                 170                 175

Ile Ala Lys Lys Tyr Asn Asn Tyr Val Tyr Leu Gly Met Ile Glu Asp
            180                 185                 190

Gln Thr Pro Gly Asp Phe His Tyr Leu Asp Gly Ala Ser Val Asn Tyr
        195                 200                 205

Thr Asn Trp Tyr Pro Gly Glu Pro Arg Gly Gln Gly Lys Glu Lys Cys
    210                 215                 220

Val Glu Met Tyr Thr Asp Gly Thr Trp Asn Asp Arg Gly Cys Leu Gln
225                 230                 235                 240

Tyr Arg Leu Ala Val Cys Glu Phe
                245
```

```
<210> SEQ ID NO 13
<211> LENGTH: 148
<212> TYPE: PRT
<213> ORGANISM: Artificial Sequence
<220> FEATURE:
<223> OTHER INFORMATION: Description of Artificial Seqence: antioxidant
      peptide

<400> SEQUENCE: 13

Ala Tyr Leu Asp Glu Glu Leu Gln Thr Glu Leu Tyr Glu Ile Lys His
1               5                   10                  15

Gln Ile Leu Gln Thr Met Gly Val Leu Ser Leu Gln Gly Ser Met Leu
            20                  25                  30

Ser Val Gly Asp Lys Val Phe Ser Thr Asn Gly Gln Ser Val Asn Phe
        35                  40                  45

Asp Thr Ile Lys Glu Met Cys Thr Arg Ala Gly Gly Asn Ile Ala Val
    50                  55                  60

Pro Arg Thr Pro Glu Glu Asn Glu Ala Ile Ala Ser Ile Ala Lys Lys
65                  70                  75                  80

Tyr Asn Asn Tyr Val Tyr Leu Gly Met Ile Glu Asp Gln Thr Pro Gly
                85                  90                  95

Asp Phe His Tyr Leu Asp Gly Ala Ser Val Asn Tyr Thr Asn Trp Tyr
            100                 105                 110

Pro Gly Glu Pro Arg Gly Gln Gly Lys Glu Lys Cys Val Glu Met Tyr
        115                 120                 125

Thr Asp Gly Thr Trp Asn Asp Arg Gly Cys Leu Gln Tyr Arg Leu Ala
    130                 135                 140

Val Cys Glu Phe
145
```

```
<210> SEQ ID NO 14
<211> LENGTH: 192
<212> TYPE: PRT
<213> ORGANISM: Artificial Sequence
<220> FEATURE:
<223> OTHER INFORMATION: Description of Artificial Sequence: antioxidant
      peptide

<400> SEQUENCE: 14

Met Ser Leu Cys Ser Leu Ala Phe Thr Leu Phe Leu Thr Val Val Ala
1               5                   10                  15
```

-continued

```
Gly Ile Lys Cys Asn Val Thr Asp Val Cys Ala Gly Ser Pro Gly Ile
            20                  25                  30

Pro Gly Ala Pro Gly Asn His Gly Leu Pro Gly Arg Asp Gly Arg Asp
        35                  40                  45

Gly Val Lys Gly Asp Pro Gly Pro Pro Gly Pro Met Gly Pro Pro Gly
    50                  55                  60

Gly Met Pro Gly Leu Pro Gly Arg Asp Gly Leu Pro Gly Ala Pro Gly
65                  70                  75                  80

Ala Pro Gly Glu Arg Gly Asp Lys Gly Glu Pro Gly Glu Arg Gly Leu
                85                  90                  95

Pro Gly Phe Pro Ala Tyr Leu Asp Glu Glu Leu Gln Thr Glu Leu Tyr
            100                 105                 110

Glu Ile Lys His Gln Ile Leu Gln Thr Met Gly Val Leu Ser Leu Gln
        115                 120                 125

Gly Ser Met Leu Ser Val Gly Asp Lys Val Phe Ser Thr Asn Gly Gln
    130                 135                 140

Ser Val Asn Phe Asp Thr Ile Lys Glu Met Cys Thr Arg Ala Gly Gly
145                 150                 155                 160

Asn Ile Ala Val Pro Arg Thr Pro Glu Glu Asn Glu Ala Ile Ala Ser
                165                 170                 175

Ile Ala Lys Lys Tyr Asn Asn Tyr Val Tyr Leu Gly Met Ile Glu Asp
            180                 185                 190


<210> SEQ ID NO 15
<211> LENGTH: 92
<212> TYPE: PRT
<213> ORGANISM: Artificial Sequence
<220> FEATURE:
<223> OTHER INFORMATION: Description of Artificial Sequence: antioxidant
      peptide

<400> SEQUENCE: 15

Ala Tyr Leu Asp Glu Glu Leu Gln Thr Glu Leu Tyr Glu Ile Lys His
1               5                   10                  15

Gln Ile Leu Gln Thr Met Gly Val Leu Ser Leu Gln Gly Ser Met Leu
            20                  25                  30

Ser Val Gly Asp Lys Val Phe Ser Thr Asn Gly Gln Ser Val Asn Phe
        35                  40                  45

Asp Thr Ile Lys Glu Met Cys Thr Arg Ala Gly Gly Asn Ile Ala Val
    50                  55                  60

Pro Arg Thr Pro Glu Glu Asn Glu Ala Ile Ala Ser Ile Ala Lys Lys
65                  70                  75                  80

Tyr Asn Asn Tyr Val Tyr Leu Gly Met Ile Glu Asp
                85                  90


<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: antioxidant
      peptide

<400> SEQUENCE: 16

Thr Pro Gly Asp Phe His Tyr Leu Asp Gly Ala Ser Val Asn Tyr Thr
1               5                   10                  15

Asn Trp Tyr Pro Gly
            20
```

-continued

```
<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: antioxidant
      peptide

<400> SEQUENCE: 17

Ser Pro Gly Asp Phe Arg Tyr Ser Asp Gly Thr Pro Val Asn Tyr Thr
1               5                   10                  15

Asn Trp Tyr Arg Gly
            20
```